United States Patent
Tobin

(10) Patent No.: US 12,227,750 B2
(45) Date of Patent: Feb. 18, 2025

(54) RECOMBINANT MICELLE AND METHOD OF IN VIVO ASSEMBLY

(71) Applicant: Mozza Foods, Inc., Los Angeles, CA (US)

(72) Inventor: Cory J. Tobin, Pasadena, CA (US)

(73) Assignee: Mozza Foods, Inc., Los Angeles, CA (US)

( * ) Notice: Subject to any disclaimer, the term of this patent is extended or adjusted under 35 U.S.C. 154(b) by 0 days.

(21) Appl. No.: 18/456,080

(22) Filed: Aug. 25, 2023

(65) Prior Publication Data

US 2023/0407319 A1 Dec. 21, 2023

Related U.S. Application Data

(63) Continuation of application No. 18/075,250, filed on Dec. 5, 2022, which is a continuation of application No. 17/717,000, filed on Apr. 8, 2022, now Pat. No. 11,718,856, which is a continuation of application No. 16/741,680, filed on Jan. 13, 2020, now Pat. No. 11,326,176.

(60) Provisional application No. 62/939,247, filed on Nov. 22, 2019.

(51) Int. Cl.
C12N 15/82 (2006.01)
B01D 61/14 (2006.01)

(52) U.S. Cl.
CPC ....... *C12N 15/8202* (2013.01); *B01D 61/145* (2013.01); *B01D 61/147* (2013.01); *B01D 61/149* (2022.08); *C12N 15/8218* (2013.01); *B01D 2315/16* (2013.01)

(58) Field of Classification Search
None
See application file for complete search history.

(56) References Cited

U.S. PATENT DOCUMENTS

| | | |
|---|---|---|
| 4,518,616 A | 5/1985 | Czulak |
| 5,015,580 A | 5/1991 | Christou et al. |
| 5,159,135 A | 10/1992 | Umbeck |
| 5,378,619 A * | 1/1995 | Rogers ............... C12N 15/8222 800/300 |
| 5,491,084 A | 2/1996 | Chalfie et al. |
| 5,538,880 A | 7/1996 | Lundquist et al. |
| 5,547,870 A | 8/1996 | Datta et al. |
| 5,550,318 A | 8/1996 | Adams et al. |
| 5,591,616 A | 1/1997 | Hiei et al. |
| 5,599,670 A | 2/1997 | Jefferson |
| 5,633,435 A | 5/1997 | Barry et al. |
| 5,780,708 A | 7/1998 | Lundquist et al. |
| 5,824,877 A | 10/1998 | Hinchee et al. |
| 6,118,047 A | 9/2000 | Anderson et al. |
| 6,153,812 A | 11/2000 | Fry et al. |
| 6,160,202 A * | 12/2000 | Bustos ............ C07K 14/415 536/23.6 |
| 6,160,208 A | 12/2000 | Lundquist et al. |
| 6,194,636 B1 | 2/2001 | McElroy et al. |
| 6,232,526 B1 | 5/2001 | McElroy et al. |
| 6,288,312 B1 | 9/2001 | Christou et al. |
| 6,384,301 B1 | 5/2002 | Martinell et al. |
| 6,399,861 B1 | 6/2002 | Anderson et al. |
| 6,541,682 B1 | 4/2003 | Nehra et al. |
| 6,603,061 B1 | 8/2003 | Armstrong et al. |
| 6,632,468 B2 | 10/2003 | Morgan et al. |
| 7,417,178 B2 | 8/2008 | Huang et al. |
| 9,924,728 B2 | 3/2018 | Pandya et al. |
| 10,894,812 B1 | 1/2021 | Lanquar et al. |
| 10,947,552 B1 | 3/2021 | Lanquar et al. |
| 10,988,521 B1 | 4/2021 | Lanquar et al. |
| 11,034,743 B1 | 6/2021 | Lanquar et al. |
| 11,072,797 B1 | 7/2021 | Lanquar et al. |
| 11,076,615 B2 | 8/2021 | Pandya et al. |
| 11,142,555 B1 | 10/2021 | Lanquar et al. |
| 11,172,691 B2 | 11/2021 | Kizer et al. |
| 11,326,176 B2 | 5/2022 | Tobin |
| 11,401,526 B2 | 8/2022 | Lanquar et al. |
| 11,457,649 B2 | 10/2022 | Pandya et al. |
| 2003/0044503 A1 | 3/2003 | Morgan et al. |
| 2004/0111766 A1 | 6/2004 | Huang et al. |
| 2004/0172682 A1 * | 9/2004 | Kinney ............... A23L 11/07 800/281 |
| 2004/0216189 A1 | 10/2004 | Houmard et al. |
| 2005/0166289 A1 | 7/2005 | Chuan Chiang et al. |
| 2005/0172356 A1 | 8/2005 | Christeller et al. |
| 2010/0048464 A1 | 2/2010 | Recio Sanchez et al. |
| 2010/0223682 A1 | 9/2010 | Katz et al. |
| 2010/0313307 A1 * | 12/2010 | Herman ............ C12N 15/8251 800/312 |

(Continued)

FOREIGN PATENT DOCUMENTS

| | | |
|---|---|---|
| CN | 101305017 A | 11/2008 |
| CN | 101600358 A | 12/2009 |

(Continued)

OTHER PUBLICATIONS

Hettinga et al.: Can recombinant milk proteins replace those produced by animals? Current Opinion in Biotechnology 75:102690; pp. 1-6 (2022).

(Continued)

*Primary Examiner* — Brent T Page

(57) ABSTRACT

A method of in vivo assembly of a recombinant micelle including: introducing a plasmid into a plant cell, wherein: the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein: the recombinant casein proteins include a κ-casein and at least one of an $αS_1$-casein, an $αS_2$-casein, a β-casein; and assembling in vivo a recombinant micelle within the plant cell, wherein: an outer layer of the recombinant micelle is enriched with the κ-casein, an inner matrix of the recombinant micelle include at least one of the $αS_1$-casein, the $αS_2$-casein, the β-casein.

8 Claims, 10 Drawing Sheets

Specification includes a Sequence Listing.

(56) References Cited

U.S. PATENT DOCUMENTS

| | | |
|---|---|---|
| 2011/0293813 A1 | 12/2011 | Cavallini et al. |
| 2012/0219600 A1 | 8/2012 | Perumal et al. |
| 2013/0065824 A1 | 3/2013 | De Kort et al. |
| 2013/0295646 A1 | 11/2013 | Lejars et al. |
| 2014/0127358 A1 | 5/2014 | Brown et al. |
| 2014/0366218 A1* | 12/2014 | Li .................. C12N 15/8279 800/290 |
| 2014/0370110 A1 | 12/2014 | Perumal et al. |
| 2016/0168198 A1 | 6/2016 | Govindappa et al. |
| 2016/0257730 A1 | 9/2016 | Mayfield et al. |
| 2017/0164632 A1 | 6/2017 | Pandya et al. |
| 2017/0273328 A1 | 9/2017 | Pandya et al. |
| 2018/0291392 A1* | 10/2018 | El-Richani ......... C12N 15/8257 |
| 2019/0216106 A1 | 7/2019 | Geistlinger et al. |
| 2019/0382781 A1 | 12/2019 | Shoseyov et al. |
| 2021/0010017 A1 | 1/2021 | El-Richani et al. |
| 2021/0030014 A1 | 2/2021 | Brown et al. |
| 2021/0037849 A1 | 2/2021 | Pandya et al. |
| 2021/0115456 A1 | 4/2021 | Mason et al. |
| 2021/0198693 A1 | 7/2021 | Mason et al. |
| 2021/0235714 A1 | 8/2021 | Geistlinger et al. |
| 2022/0098259 A1 | 3/2022 | Lanquar et al. |
| 2022/0169690 A1 | 6/2022 | Lanquar et al. |
| 2022/0290167 A1 | 9/2022 | Tobin et al. |
| 2022/0325292 A1 | 10/2022 | Tobin |
| 2022/0372504 A1 | 11/2022 | Lanquar et al. |
| 2022/0378058 A1 | 12/2022 | Ghandi et al. |
| 2022/0378723 A1 | 12/2022 | Wang et al. |
| 2023/0000100 A1 | 1/2023 | Zahn et al. |
| 2023/0034320 A1 | 2/2023 | Aharoni et al. |
| 2023/0141532 A1 | 5/2023 | Gibson et al. |
| 2023/0203556 A1 | 6/2023 | Lanquar et al. |
| 2023/0212594 A1 | 7/2023 | Tobin |

FOREIGN PATENT DOCUMENTS

| | | |
|---|---|---|
| CN | 102883623 A | 1/2013 |
| EP | 4060045 A1 | 9/2022 |
| WO | WO-2013148331 A1 | 10/2013 |
| WO | WO-2021050759 A2 | 3/2021 |
| WO | WO-2021101647 A1 | 5/2021 |
| WO | WO-2023002061 A2 | 1/2023 |

OTHER PUBLICATIONS

Kim et al.: Effects of proteome rebalancing and sulfur nutrition on the accumulation of methionine rich δ-zein in transgenic soybeans. Frontiers in Plant Science, vol. 5 Article 633 (1-12) 2014.

PCT/US2020/056449 International Search Report and Written Opinion dated Feb. 3, 2021.

Philip et al.: Processing and localization of bovine beta-casein expressed in transgenic soybean seeds under control of a soybean lectin expression cassette. Plant Sci. 161(2):323-335 doi:10.1016/s0168-9452(01)00420-4 (2001).

Sood et al.: Formation of Reconstituted Casein Micelles with Human β-Caseins and Bovine κ-Casein. J. Dairy Sci. 85:472-477 (2002).

U.S. Appl. No. 17/717,000 Final Office Action dated May 10, 2023.

U.S. Appl. No. 17/717,000 Non-Final Office Action dated Feb. 1, 2023.

U.S. Appl. No. 17/717,000 Notice of Allowance dated Jun. 14, 2023.

QI: Studies of casein micelle structure: the past and the present. Lait 87 (2007) 363-383 (2007) [Article published by EDP Sciences and available at http://www.lelait-journal.org ].

Co-pending U.S. Appl. No. 17/890,172, inventor Tarshis; Adam, filed on Aug. 17, 2022.

U.S. Appl. No. 63/281,069, inventors Tobin; Cory J. et al., filed on Nov. 18, 2021.

U.S. Appl. No. 63/331,460, inventors Tobin; Cory J. et al., filed on Apr. 15, 2022.

U.S. Appl. No. 63/376,223, inventors Johnson; Brady et al., filed on Sep. 19, 2022.

* cited by examiner

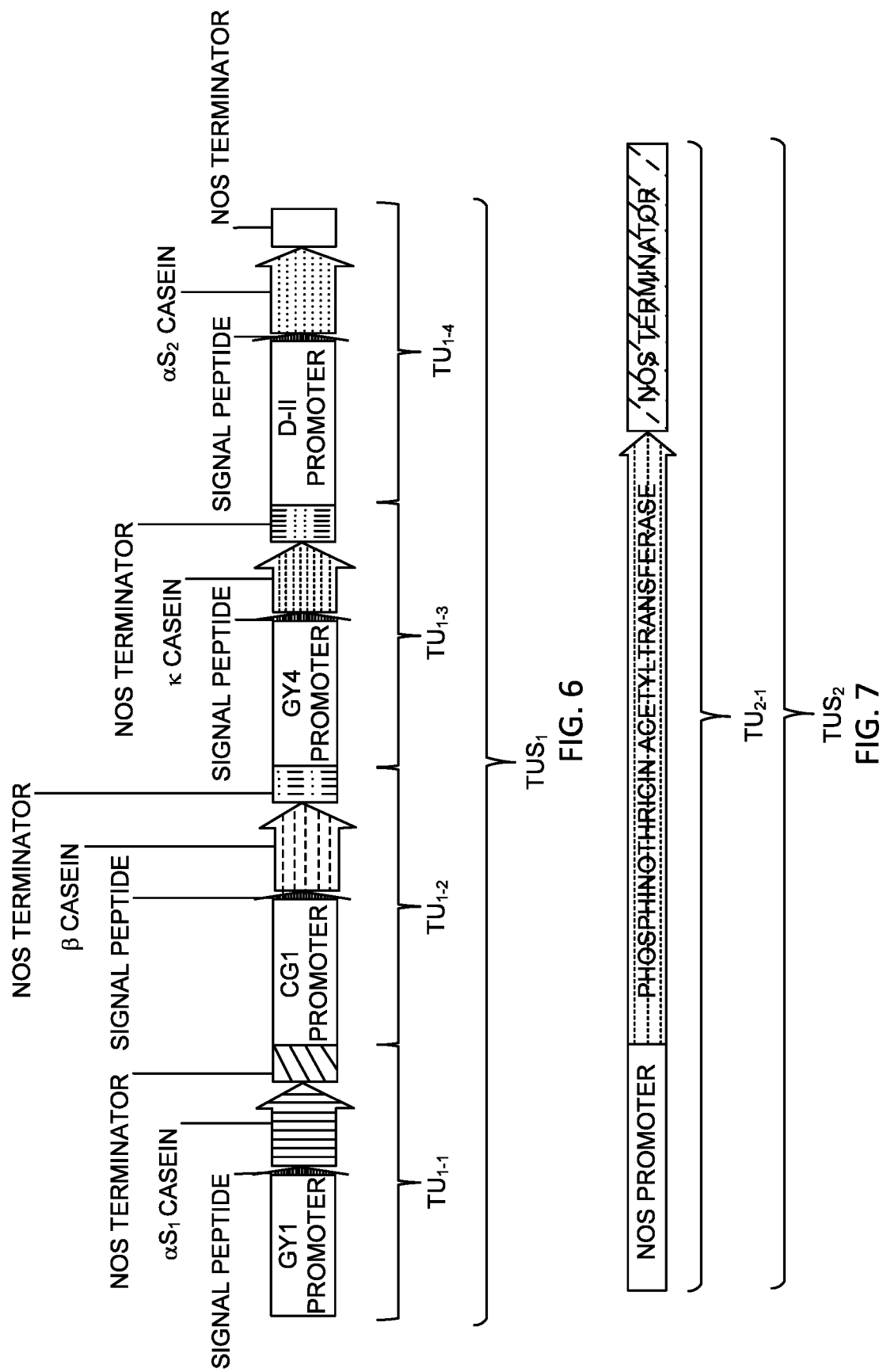

SEQUENCE LISTING

```
Sequence total quantity: 35
SEQ ID NO: 1            moltype = DNA  length = 600
FEATURE                 Location/Qualifiers
source                  1..600
                        mol_type = other DNA
                        organism = synthetic construct
misc_feature            1..600
                        note = Codon optimized
SEQUENCE: 1
aggcccaagc acccatcaa gcatcagggg ttgccacagg aagtcctcaa tgaaaatctg   60
ctgaggttct tcgtggctcc tttcccagaa gttttcggaa aggaaaaagt taacgagctc  120
agcaaagaca tcggctctga atccaccgaa gaccaagcaa tggaggacat taagcaaatg  180
gaagctgaga gtatatcctc atccgaagaa atcgtcccaa acagcgtaga acaaaagcat  240
attcagaaag aagatgttcc tagtgaaaga tacctcgggt atttggagca acttctgaga  300
ctgaaaaagt acaaagtgcc ccagctcgag atcgttccaa actccgccga agaacgtctg  360
catagtatga aggaggggat acatgcacaa cagaaggaac ccatgatcgg agttaaccag  420
gaactcgctt acttctaccc tgaactcttc aggcagtttt atcagcttga cgcttatccc  480
tccggtgctt ggtactatgt accacttgga acacaataca cagacgcacc atcattttct  540
gacatacccca accctatcgg gtctgagaac agtgaaaaaa caacaatgcc tctgtggtaa  600

SEQ ID NO: 2            moltype = DNA  length = 510
FEATURE                 Location/Qualifiers
source                  1..510
                        mol_type = other DNA
                        organism = synthetic construct
misc_feature            1..510
                        note = Codon optimized
SEQUENCE: 2
caggagcaga accaagaaca acctatcagg tgcgaaaagg atgagaggtt ctttttccgat   60
aaaattgcaa agtacattcc tattcaatat gtactgtctc gctaccccag ttatggactt  120
aactactacc aacagaaacc cgttgccctt ataaacaatc agttcctccc ttatccttac  180
tatgcaaagc ctgctgccgt gcgtagtccc gcacagattc tccagtggca ggttctcagc  240
aatactgttc ccgcaaaaag ctgtcaggct caacctacta ctatggcacg tcatcctcac  300
ccccatttga gctttatggc catccctcca aagaagaacc aagataagac tgaaatccca  360
actataaaca caatcgcatc cggggagcct acctctactc ccactattga ggctgtcgaa  420
tctactgttg caactttgga agctagtccc gaagtcaccg agagcccccc tgagatcaac  480
accgtacagg ttacatctac cgctgtatga                                   510

SEQ ID NO: 3            moltype = DNA  length = 630
FEATURE                 Location/Qualifiers
source                  1..630
                        mol_type = other DNA
                        organism = synthetic construct
misc_feature            1..630
                        note = Codon optimized
SEQUENCE: 3
agggagctgg aagagctgaa cgtccctggc gaaatagtag agtccctcag ctcatcagaa   60
```

```
gagtccatta ctcgtattaa caaaaagatt gaaaagtttc agtcagaaga gcaacaacag    120
actgaggacg aactccaaga caagattcac cctttcgcac agacacagag tctggtctac    180
ccatttcctg gtccattcc caattccctt cccagaata tacctcccct cacccagact    240
cctgtggtgg tccccccatt cctccaacca gaggttatgg gtgtttctaa agtcaaagaa    300
gcaatggccc ctaagcacaa agagatgcca ttccccaagt atccgttga gccctttacc    360
gagtctcaga gccttacact gaccgacgta gaaaatctcc atctcccact cccattgttg    420
caatcttgga tgcaccagcc ccatcagcct ttgcccccta ctgtcatgtt tccccccag    480
agtgttctgt ccttgagcca aagcaaagtg ctccctgtgc cccagaaagc cgtacccttat  540
ccccaaagag acatgccaat acaggccttt ttgctctacc aggagcctgt tctcggtccc    600
gtaagaggcc ctttccctat catcgtgtag                                    630

SEQ ID NO: 4              moltype = DNA   length = 624
FEATURE                   Location/Qualifiers
source                    1..624
                          mol_type = other DNA
                          organism = synthetic construct
misc_feature              1..624
                          note = Codon optimized
SEQUENCE: 4
aaaaacacta tggagcacgt aagctcatcc gaggagagta taatctccca ggaaacatat    60
aaacaagaaa aaaatatggc aattaaccca tccaaggaaa acctgtgttc caccttttgt    120
aaggaagtcg tgcgtaatgc taatgaagaa gagtattcaa tcggctccag ttcagaggag    180
tctgcagaaa tagccacaga ggaggttaag attactgttg atgataaaca ctaccaaaag    240
gcccttaacg agataaatca gttctatcaa aaatttcctc aatatttgca atacttgtat    300
cagggaccta ttgttctcaa tccttgggat caggttaagc gtaacgccgt accaattaca    360
ccaactctca acagggagca gctcagcacc tccgaggaaa actccaaaaa gacagtggat    420
atggagtcaa ctgaggtctt cacaaaaaag acaaagctca ccgaggaaga gaagaacaga    480
ctcaactttt tgaaaaaaat atcacaaaga taccaaaagt ttgcactgcc caatatctc    540
aagactgttt accaacacca aaaggctatg aagccctgga ttcaaccaaa gaccaaagtc    600
ataccctacg tgaggtattt gtaa                                          624

SEQ ID NO: 5              moltype = DNA   length = 612
FEATURE                   Location/Qualifiers
source                    1..612
                          mol_type = other DNA
                          organism = synthetic construct
misc_feature              1..612
                          note = Codon optimized
SEQUENCE: 5
cgtccgaaac atccaatcaa gcaccaaggc ctcccacagg aggtcctcaa cgaaaacctt    60
ttacgttttt ttgtggcacc cttccctgag gtcttcggaa aggaaaaagt gaatgaactt    120
tcaaaggaca ttggcagcga atccacggaa gaccaggcga tggaggatat taagcagatg    180
gaggctgaaa gtattagctc ttccgaggag atagttccta ttccgtgga acaaaagcac    240
attcaaaaag aggatgtccc gagtgagaga tacctgggct atctcgaaca gcttctgaga    300
ctaaaaaagt ataaggtccc gcaactgaaa attgttccaa atagcgccga agaaaggtta    360
cattccatga agaaggcat tcatgctcag caaaaggaac ctatgatcgg agtaaaccag    420
gaactttgcct attttaccc ggagttgttc cgtcagttct atcagttgga tgcatacca    480
tcagggcat ggtactatgt acctctcggt acccaataca cggacgctcc ttctttctcc    540
gatataccca atcccatagg tagcgaaaac tctgagaaaa caactatgcc cctctggcat    600
gacgaacttt ag                                                       612

SEQ ID NO: 6              moltype = DNA   length = 522
FEATURE                   Location/Qualifiers
source                    1..522
                          mol_type = other DNA
                          organism = synthetic construct
misc_feature              1..522
                          note = Codon optimized
SEQUENCE: 6
caagaacaga atcaggagca acccattagg tgtgagaagg acgaaaggtt ttttcagac    60
aaaatcgcga aatacatacc tattcagtac gttctcagca gataccctag ttatggactt    120
aactactacc agcaaaagcc tgtggcattg ataaataacc agttccttcc gtacccgtac    180
tatgcgaaac cggcagcgt acgaagccca gcccagattt tgcaatggca ggtattgagt    240
aacaccgtcc cggcgaaaag ttgtcaagcg caaccgacca caatggcccg acaccccgat    300
ccacatctca gcttcatggc aatcccaccc aagaaaaacc aagataaaac tgaaataccg    360
acaataaaca ctatagcttc aggcgagcca actagcacac ccactattga gcggtagag    420
agtacggtcg caaccctaga ggcaagcccg gaagtgactg aatctccgcc ggaaattaac    480
accgtccagg taacctcaac agcggttcat gacgaactct ag                      522

SEQ ID NO: 7              moltype = DNA   length = 639
FEATURE                   Location/Qualifiers
source                    1..639
                          mol_type = other DNA
                          organism = synthetic construct
misc_feature              1..639
                          note = Codon optimized
SEQUENCE: 7
cgtgaactag aagagcttaa tgtgcctggt gagatagtcg aaagtttgtc cagctcagaa    60
gaatcaatta cacgtatcaa caaaaaaata gaaaagtttc aatctgagga caacaacag    120
```

-continued

```
acagaggacg aattacaaga taaaatacac ccatttgctc agacgcaaag cttagtctat    180
ccattcccag gaccaattcc gaatagctta cctcaaaaca tcccgccgct cacgcagacc    240
cctgtagtcg tgccgccgtt tttacaaccc gaggtcatgg gcgtcagcaa ggtaaaagag    300
gcaatggctc ctaagcataa ggagatgcct ttccctaaat atcccgtcga gccttttcacc   360
gagagccaat ctttaacctt aacgacgta gagaacctac atcttcctct accactgtta    420
caatcctgga tgcatcagcc gcaccaacct cttccccctca cagtaatgtt ccccccgcag    480
tccgtcctat ctctctctca atccaaggtc ctaccagttc ctcagaaggc tgtccctac     540
cctcagcgag acatgccgat ccaggctttc ttgctatacc aagagccggt actaggccct    600
gtccgagggc cgtttccgat aattgtccac gatgaactt                            639

SEQ ID NO: 8             moltype = DNA  length = 636
FEATURE                  Location/Qualifiers
source                   1..636
                         mol_type = other DNA
                         organism = synthetic construct
misc_feature             1..636
                         note = Codon optimized
SEQUENCE: 8
aaaaacacta tggagcatgt gagcagctct gaggagtcca ttatatccca ggaaacatat    60
aaacaagaaa agaacatggc tattaacccg tcaaaggaga atctgtgttc cacgttctgt    120
aaggaagtgg tgaggaacgc taatgaggaa gagtactcaa tcggcagttc atccgaagaa    180
tctgctgagg tggcgacaga agaagttaag attactgtcg agacaaaca ctaccagaag    240
gccctaaatg agataaatca attttatcag aagttcccgc agtatttgca atatctatat    300
caggggccaa tcgttctcaa tccatgggat caggtgaaaa gaaacgcagt acctatcaca    360
cctacgctga cagggaaca actgagcacc tctgaggaaa actcaaaaaa gaccgtagac    420
atggagtcca ctgaggtctt taccaagaaa acaaagctaa gaggaggaa gaaaaatcga    480
ctgaattttc tgaagaaaat cagccagcgt tatcaaaagt tcgctctccc tcagtaccta    540
aagacggtat atcaacacca aaaagctatg aagccgtgga tacagcccaa gacgaaagtg    600
attccatacg tgcgttatct tcacgatgaa ttatag                              636

SEQ ID NO: 9             moltype = DNA  length = 675
FEATURE                  Location/Qualifiers
source                   1..675
                         mol_type = other DNA
                         organism = synthetic construct
misc_feature             1..675
                         note = Codon optimized
SEQUENCE: 9
atgggttact ctaagacact ggttgctggc ctgtttgcca cacttctgct ggctcccgtg    60
gtgttggcca ctgatcccga tccacttcaa gacttctgcg tagctgacct cgatggtaaa    120
gctgtaagtg tcaacggcca tccttgcaag ccaatgtcaa aagcagggga cgatttcttg    180
ttttcctcta aactggctaa agctggtaac acttccaccc ctaatggtag tgctgtgaca    240
gagcttgacg ttgcagaatg gcccggaact aacactttgg gagtcagtat gaaccgtgtc    300
gattttgccc ctggggggac aaatccacct catattcacc cacgtgccac agaaattggc    360
atagtcatga gggcgaact tctcgtgggc atccttggca gcttggactc aggcaataaa    420
cttattccc gcgtagtcag ggccggtgag acttttcttga ttcccagggg actgatgcac    480
ctgcagttca acgtaggaaa aactgaagcc agtatggtag tctccttcaa ttctcaaaat    540
cccggtattg tgttcgtccc cctcactctg ttctcctcta acccccaat cccaactccc    600
gtacttacca aggctcttag agtcgaggct ggagttgtag agctgttgaa gtcaaagttt    660
gcagccggat tttaa                                                      675

SEQ ID NO: 10            moltype = DNA  length = 176
FEATURE                  Location/Qualifiers
source                   1..176
                         mol_type = other DNA
                         organism = synthetic construct
misc_feature             1..176
                         note = This sequence has elements from Arabidopsis thaliana
                         and Glycine max.
SEQUENCE: 10
agagccagag agcagcctca gcaaaacagg tcgtgatatg attcaattag cttccgactc    60
attcatccaa ataccgagtc gccaaaattc aaactagact cgttaaatga atgaatgatg    120
cggtagacaa attggatcat tgattctctt tgatttgctg aggctgctct ctggct        176

SEQ ID NO: 11            moltype = DNA  length = 1644
FEATURE                  Location/Qualifiers
source                   1..1644
                         mol_type = genomic DNA
                         organism = Glycine max
SEQUENCE: 11
atggcgtcaa ttacttttc tcttcttcaa tttcatcgtg ctcctattct tctgctaatt    60
ctgctcgcgg gttcggtca ctgccatatt ccgtcaaccc tcgaaggtcc ctttgatccc    120
gtcaccgttc cgttcgaccc cgccttgcgc ggcgtcgccg tcgacttgcc ggaaaccgat    180
cctcgagttc gccgccacgt ccggggtttc gagcccgaac agattttcggt ttctctctct    240
acctcccatg actccgtttg gatatcttgg gttacagggg agttccaaat aggtctcgac    300
atcaagcctt tagaccctaa aactgtatca agtgttgttc aatatggaac ttcaagatt    360
gaattagtgc atgaagctag aggccagtct ctcatctaca accagctcta tccttttgaa    420
ggccttcaga attacacatc tggaatcatc catcacgttc aactcaaagg attggaacca    480
agcacactat actattatca atgtggagat ccttcattgc aagccatgag tgatatatac    540
```

```
tatttcagga ccatgccaat ttctggttca aagagctacc caggcaaagt agctgtagta    600
ggagatcttg gtcttactta taatacaact actaccatcg gtcacctgac tagtaatgaa    660
cctgatcttc ttctattgat tggtgatgta acctacgcga atctgtacct cacaaatgga    720
actggctctg attgttatag ttgctcgttt ccactaactc ctatacatga aacctaccag    780
cctcgatggg attattgggg aaggtttatg cagaatctag tttctaacgt tccaataatg    840
gtggtagaag gaaatcatga aatagaaaaa caggctgaaa acaggacatt tgtggcctac    900
agttctaggt ttgcattccc ctctcaagaa agtggatctt catctacatt ctactattct    960
ttcaatgctg gaggcattca ttttattatg cttggggctt atattaacta tgataaaacg   1020
gctgaaccat acaagtggtt ggagagagat ctggaaaatg ttgatagatc aataactcac   1080
tggcttgtag ttacttggca tccaccatgg tatagttctt atgaagccca ttacagagaa   1140
gcagagtgca tgagggtgga gatggaggac ctattatacg catatggtgt ggatataata   1200
tttaatggac atgttcatgc ctatgagagg tcaaaccgag tttacaatta caatttagat   1260
ccatgtggtc ctgtatatat tacagttggg gatgggggca acagagagaa gatggcaatc   1320
aaattcgcag acgagcctgg tcattgtccc gatccattaa gtactcctga tccttatatg   1380
ggtggctttt gtgcaacaaa ttttacgttt ggtacaaaag tgagtaagtt ttgttgggat   1440
cgccagccag attacagtgc tttcagaaa  agtagctttg gctatgggat tctagaggtg   1500
aaaaatgaaa cttgggcttt gtggagttgg tatcgtaatc aggactctta caaggaagtt   1560
ggggatcaaa tttacatagt gagacaacct gatatatgcc ccatccatca aagggtgaac   1620
atagattgca ttgcttcgat ataa                                          1644

SEQ ID NO: 12           moltype = DNA  length = 1284
FEATURE                 Location/Qualifiers
source                  1..1284
                        mol_type = other DNA
                        organism = synthetic construct
misc_feature            1..1284
                        note = Codon optimized
SEQUENCE: 12
atggtcccac ttgcaagtac caccaccggc accgggaccg ctaccggtac atcaactgca     60
gccgaacctt ccgccactgt gccatttgca agtacagatc caaaccccgt cctctgtgaa    120
gaaacatcag atccagcact tgtgaagcct gagcgcaatc agctcggggc tactatccag    180
ggtcctgata tctgcctat cgatttgcag aacccagatc tgttggctcc tcctaccact    240
gaccatggtt ttgtagggaa tgcaaagtgg ccattctcat ttagcaaaca aagacttcaa    300
accggcgggt gggcaagaca gcaaaatgaa gtcgttcttc ctctcgctac caatctgct    360
tgtactaata tgaggctgga agccggggca attagagagc tccattggca taaaaacgcc    420
gaatgggctt acgtgttgaa aggtagtacc cagatttccg ctgtggacaa tgagggaagg    480
aactacatca gtactgtcgg tccaggcgat ctgtggtatt tcccccctgg aatccccccac   540
tcccttcaag ccaccgccga cgaccctgag gggtccgagt tcattttggt gtttgatagt    600
ggagccttca atgatgacgg aaccttttctt ctcaccgact ggctgagtca cgtccctatg   660
gaagtcattc tgaaaaattt tagggccaag aaccccgctg cttggtccca tatacccgcc    720
cagcagttgt atatttttcc cagtgagcct ccgccgata accagccaga ccccgtcagt    780
ccccaggggaa ccgtccccct cccatattcc tttaatttct caagtgtgga acctaccccag  840
tactcaggggg gtaccgccaa aattgccgat agtacaactt ttaatattag tgtcgcaagt   900
gcagtggcag aagtaacagt tgagcctgga gcactcagag aacttcattg gcaccccacc    960
gaagatgagt ggacattctt catctcaggc aacgcacgcg tgactatttt cgcagcacaa   1020
agtgtagcca gtacttttga ttaccagggc ggagatatag catatgttcc cgccagtatg   1080
ggccactacg tcgagaacat agggaatact accttgacct accttgaagt gttcaacaca   1140
gacagattcg ccgacgtgag tcttagccaa tggctggccc tcacacctcc atccgttgtt   1200
caagcacacc tgaacctcga tgacgaaact ctggccgaac ttaagcagtt cgccaccaag   1260
gctacagtag tgggccccgt gaat                                          1284

SEQ ID NO: 13           moltype = DNA  length = 1024
FEATURE                 Location/Qualifiers
source                  1..1024
                        mol_type = genomic DNA
                        organism = Glycine max
SEQUENCE: 13
aaagaagtaa atcatgagct tttccaactc aacatctatt tttttctct caacctttt      60
cacatcttaa gtagtctcac cctttatata taaacttat ttcttacctt ttacattatg     120
taacttttat caccaaaacc aacaactttta aatttttatt aaatagactc cacaagtaac   180
ttgacactct tacattcatc gacattaact tttatctgtt ttataaatat tattgtgata   240
taatttaatc aaaataacca caaactttca taaaaggttc ttattaagca tggcatttaa    300
taagcaaaaa caactcaatc actttcatat aggaggtagc ctaagtacgt actcaaaatg   360
ccaacaaata aaaaaaagt tgctttaata atgccaaata aataataa aacacttaca      420
acaccggatt ttttttaatt aaaatgtgcc atttaggata aatagttaat attttttaata  480
attatttaaa aagccgtatc tactaaaatg atttttattt ggttgaaaat attaatatgt   540
ttaaatcaac acaatctatc aaaattaaac taaaaaaaaa ataagtgtac gtggttaaca   600
ttagtacagt aatataagag gaaaatgaga aattaagaaa ttgaaagcga gtctaatttt   660
taaattatga acctgcatat ataaaaggaa agaaagaatc caggaagaa agaaatgaaa   720
ccatgcatgg tccctcgtc atcacgagtt tctgccattt gcaatagaaa cactgaaaca     780
cctttctctt tgtcacttaa ttgagatgcc gaagccacct cacaccatga acttcatgag    840
gtgtagcacc caaggcttcc atagccatgc atactgaaga atgtctcaag ctcagcaccc    900
tacttctgtg acgtgtccct cattcacctt cctctcttcc ctataaataa ccacgcctca    960
ggttctccgc ttcacaactc aaacattctc tccattggtc cttaaacact catcagtcat   1020
cacc                                                                1024

SEQ ID NO: 14           moltype = DNA  length = 1055
FEATURE                 Location/Qualifiers
source                  1..1055
```

```
                        mol_type = genomic DNA
                        organism = Glycine max
SEQUENCE: 14
tttacaataa atactcaatt tatctttcac aatcaaaaga ttgagatgtt gtaagatctc    60
cgataaatata cttatatctt ttcatttatt acgttttcaa atttgaattt taatgtgtgt   120
tgtaagtata aatttaaaat aaaaatmaaa acaattatta tatcaaaatg gcaaaaacat   180
ttaatacgta ttatttaaga aaaaaatatg taataatata tttatatttt aatatctatt   240
cttatgtatt ttttaaaaat ctattatata ttgatcaact aaaatatttt tatatctaca   300
cttattttgc atttttatca atttcttgc gttttttggc atatttaata atgactattc    360
tttaataatc aatcattatt cttacatggt acatattgtt ggaaccatat gaagtgtcca   420
ttgcatttga ctatgtggat agtgttttga tccaggcctc catttgccgc ttattaatta   480
atttggtaac agtccgtact aatcagttac ttatccttcc tccatcataa ttaatcttgg   540
tagtctcgaa tgccacaaca ctgactagtc tcttggatca taagaaaaag ccaaggaaca   600
aagaagaca aaacacaatg agagtatcct ttgcatagca atgtctaagt tcataaaatt   660
caaacaaaaa cgcaatcaca cacagtggac atcacttatc cactagctga tcaggatcgc   720
cgcgtcaaga aaaaaaaact ggaccccaaa agccatgcac aacaacacgt actcacaaag   780
gtgtcaatcg agcagcccaa aacattcacc aactcaaccc atcatgagcc cacacatttg   840
ttgtttctaa cccaacctca aactcgtatt ctcttccgcc acctcatttt tgtttatttc   900
aacacccgtc aaactgcatg ccaccccgtg gccaaatgtc catgcatgtt aacaagacct   960
atgactataa atatctgcaa tctcggccca ggttttcatc atcaagaacc agttcaatat  1020
cctagtacac cgtattaaag aatttaagat atact                             1055

SEQ ID NO: 15          moltype = DNA  length = 1045
FEATURE                Location/Qualifiers
source                 1..1045
                        mol_type = genomic DNA
                        organism = Glycine max
SEQUENCE: 15
ccttctcatc ctctctgaat attttgagtg ctcttcctag ttatctagta atgcatgaaa    60
ttaaacttac taaatgtttc ttcaatttaa agaaataatt gtttatctgt ttcaatttt    120
ttaagagaat tttaaaaaga taattgtttc ggggagagag atataaaaaa gaaaagggag   180
aaatattaaa atgtactaaa taatatgata agaaaagaga gaaaaataaa agagaaaatt   240
tgtatatagt tataattatt catgtaataa ggattcatct ctcaactgaa aatatactta   300
atgcagaaga aaaaatcatt atttacaaac gttgagtctt gagtgggaaa agaggaggcg   360
ccgttactat acaatataag atcatagtac tgacaaaatg cacagtaaaa cagttcaaat   420
tgagaaggat tcttaacaca ccatagtatt taatatatat ctttacagag acaattatgc   480
tggaggattc aggcaaagat tatatattgt ggatttgttt tttaataatt aacgcatcat   540
atgaaagatc gatgatatat actaatggtt ataagaaaaa tatttaacag tttctataac   600
ctttttcttt tatctttttac tgtaatatta tttattttat ttcacatttt taatcagctt   660
atctcatttta taaacgaaat tgtataaaaa tatacatgat gaactgaata gaacaatatt   720
gatctgatat tctcatattg tataagagga tagactttga gacgcggaga atctgtagga   780
ggggaccatt cagagtgcct ccaattttgg tgttgttcat tgtaccattg caaatataaa   840
cgaagcatgc atgcttatgt atgaggtgta acaaaattgg aaacaatagc catgcaaggt   900
gaagaatgtc acaaactcag caacccttat tcattgacgt gtccctcagt cactctcctc   960
tcataacctat aaatcaccac tcctcatgtt ctttccaatt caccaactcc ttcaaactta  1020
attattaaca cttccttagt tcaat                                         1045

SEQ ID NO: 16          moltype = DNA  length = 1186
FEATURE                Location/Qualifiers
source                 1..1186
                        mol_type = genomic DNA
                        organism = Glycine max
SEQUENCE: 16
gtctatttgc atgttcttct gcatggtatt aagaagttct tagagaatta atctaagtac    60
atttttttg gtctggatca gacatcatat ggatgctttc aaattcatgc gttggagatt   120
aattttactc ataataggta attatattaa ttaaaagaaa ttttacataa aaatacaaca   180
taaattattc cattaaatat attattccct gtgactacaa tgagataatc taagtgtatt   240
tgaaagtgga acagtagaaa ttataaaaat tgcaatgagt tgaataaaaa aggttggatt   300
aagaaagtaa tctaagtaca tttggaagtg gaatagtaga aataaaatta aatgagttga   360
aattgaaaat aattaaaaaa agtagggcta agaaatttct ccttcaactt catgatagca   420
aatattccat taggccattt gtagtttatg aatgagtata tataatcatg attttaggaa   480
ttcgatctgc tcgacacaac cgtgttacac tttttttaaa atgtcatcat aaaaataaaa   540
aataaaagac atgttataat taagaataag gtgatcagta taaaaataag taattttggg   600
aaatattaaa gttcaaaaaa gaactattga aagaaagaat attattattt aaaaagagaa   660
aagaaaatga tgaaatgcta ttttcagtta agaaaatmaa gaaaaaaaaa tacaaagaat   720
aattcaatgc tggggctgta tatatgttta agatgataat taatttttt ttaaaaaaaa   780
gataagaatt aaatattttc tcctttaatt tctgaatcac ggttttggtt ctgataagac   840
actgattagt cacccatcaa atataagaa ctaattctcc tattctattt caaaattttg    900
attatacttta gattaatttt ctaatatact tggacctgtt tttcatgcag aagatgcaga   960
tatagctaga cagcacctag taatcgtgga accaacacca atgtccatat catgcatgtg  1020
tgccaccttt caaatgtaat ccagtagtaa aaaaagccat gacatgtaac tccacgcacg  1080
agtaaaactc tcagagtac ctctcgtttc atatctgcaa atcctctaat ataaataact  1140
cacttcacgg gttctttct cttcacagca aaaacaatta ataaag                  1186

SEQ ID NO: 17          moltype = DNA  length = 179
FEATURE                Location/Qualifiers
source                 1..179
                        mol_type = genomic DNA
                        organism = Glycine max
```

```
SEQUENCE: 17
ctacgaaggg cgttgcggtt gagggtgcag cgagagaggg caacaccggc acactggaat    60
ggcttgttgt tagggttcca tgtctcaatg agccctcctt ctgactctat acggttatcc   120
ggtttgaggg cattgagttt ttggatctgg cactcgtttt gctgaggctg ctctctgga    179

SEQ ID NO: 18              moltype = DNA   length = 1000
FEATURE                    Location/Qualifiers
source                     1..1000
                           mol_type = genomic DNA
                           organism = Glycine max
SEQUENCE: 18
aaaatagtgt ttgattttt gacacattat taagtgtttt atttttaagt ttaaaagcat      60
tggtatcctt tcataaaagg aggtaatctt atttaagtca aggagaatta ttatgggaaa   120
taaaacctt ttttttaaag tgtttaatat aattatatac tcaaaattcg attttatgatt   180
aaatctaagt gacatttaaa aaaaattagt gtgaaaataa tttatatata attttgaaaa   240
atttatcatt aattttttt tataaataaa tgttaattta ttagtttta ttataaatgt    300
gaatagaatg gattcgaagc agcaatttct ctctttctcc ttttccatgc caaccttata   360
tatggtgacg aactgcatat acagtaaaac agttcaaatt gagaaagatt ttaaacatca   420
tagtatttga tatatatctt ttacagagac aattatgctg caggagttag ataagattat   480
tgtggatgtc attttctttt ttaatattta acgcattata taaaagatga tatagtatgg   540
ttataaaaaa attatttaac agtttataaa accttttttt ttatctttta cagtaatatt   600
atttatttta tttcacattt ttttcatatc cttatctaat tataaagga aattaattgt     660
ataaaaaaaa tatgatgcac tgaatagaat gctgatctta ttgtataagg aggatagaat   720
ttgagacgcg gagaatctgt agaggggggac cattcagggt gcctgcaatt ttggtgttgt   780
tcatgtacgg ttgcagatat aaacgaagca tagcttatgt atgaggtgta acaaaattgg   840
aaacaatagc catgcaaggt gaagaatgtc accaactcag aaaacccttct tcattgacgt   900
gtccctcact cactctcctc tcttcactat aaatcgccat caatcgccac tcttcgtgtt ctccacttca 960
ccaactcctt caaacttatt aacactttcc ttagttcaat                        1000

SEQ ID NO: 19              moltype = DNA   length = 146
FEATURE                    Location/Qualifiers
source                     1..146
                           mol_type = genomic DNA
                           organism = Glycine max
SEQUENCE: 19
tttctgtctc atttggcatt gcgtattggg aaaagcagaa ccccagtcac aacaagtgcc    60
tccgaagttg caatagcgag aaagactcct acaggaacca agcatgccac gctcgttgca   120
acctccttaa ggtggaggaa gaagaa                                       146

SEQ ID NO: 20              moltype = DNA   length = 150
FEATURE                    Location/Qualifiers
source                     1..150
                           mol_type = genomic DNA
                           organism = Glycine max
SEQUENCE: 20
ttcttcttcc tccaccttaa ggaggttgca acgagcgtgg catgcttggt tcctgtagga    60
gtcttctcg ctattgcaac ttcggaggca cttgttgtga ctggggttct gcttttccca   120
atacgcaatg ccaaatgaga cagaaactga                                   150

SEQ ID NO: 21              moltype = DNA   length = 114
FEATURE                    Location/Qualifiers
source                     1..114
                           mol_type = genomic DNA
                           organism = Glycine max
SEQUENCE: 21
atcgagaatt ttaaggttga gtgtcctaat gtgaagtaca ccgagactga gattcagtcc    60
gtgtacaact acgaaaccac cgaacttgtt cacgagaaca ggaatggcac ctat         114

SEQ ID NO: 22              moltype = DNA   length = 114
FEATURE                    Location/Qualifiers
source                     1..114
                           mol_type = genomic DNA
                           organism = Glycine max
SEQUENCE: 22
ataggtgcca ttcctgttct cgtgaacaag ttcggtggtt tcgtagttgt acacggactg    60
aatctcagtc tcggtgtact tcacattagg acactcaacc ttaaaattct cgat         114

SEQ ID NO: 23              moltype = DNA   length = 1081
FEATURE                    Location/Qualifiers
source                     1..1081
                           mol_type = genomic DNA
                           organism = Glycine max
SEQUENCE: 23
acaaaattaa gaactgatac atccttgtttt ttgtcactga agataaacac gtgatctttg    60
gcaaaacata aaggccaaca aaacaaaactt gtctcatccc tgaatgattc gaatgccatc  120
gtatgcgtgt cacaaagtgg aatacagcaa tgaacaaatg ctatcctctt gagaaaagtg   180
aatgcagcag cagcagcaga ctagagtgct acaaatgctt atcctcttga gaaagtgaa    240
tgcagcggca gcagacctga gtgctatata caattagaca cagggtctat taattgaaat   300
tgtcttatta ttaaatatt cgtttatat taattttta aattttaatt aaatttatat     360
```

```
atattatatt taagacagat atatttattt gtgattataa atgtgtcact ttttcttttta    420
gtccatgtat tcttctattt tttcaattta actttttatt tttatttta  agtcactctt     480
gatcaagaaa acattgttga cataaaacta ttaacataaa attatgttaa catgtgataa     540
catcatattt tactaatata acgtcgcatt ttaacgtttt tttaacaaat atcgactgta     600
agagtaaaaa tgaaatgttt gaaaaggtta attgcatact aactattttt tttcctataa     660
gtaatctttt ttgggatcaa ttgtatatca ttgagatacg atattaaata tgggtacctt     720
ttcacaaaac ctaacccttg ttagtcaaac cacacataag agaggatgga tttaaaccag     780
tcagcaccgt aagtatatag tgaagaaggc tgataacaca ctctattatt gttagtacgt     840
acgtatttcc ttttttgttt agttttttgaa tttaattaat taaaatatat atgctaacaa    900
cattaaattt taaatttacg tctaattata tattgtgatg tataataaat tgtcaacctt     960
taaaaattat aaaagaaata ttaatttga  taaacaactt tgaaaagta  cccaataatg    1020
ctagtataaa taggggcatg actccccatg catcacagtg caatttagct gaagcaaagc    1080
a                                                                    1081

SEQ ID NO: 24           moltype = DNA   length = 179
FEATURE                 Location/Qualifiers
source                  1..179
                        mol_type = genomic DNA
                        organism = Glycine max
SEQUENCE: 24
tccagagagc agcctcagca aaacgagtgc cagatccaaa aactcaatgc cctcaaaccg     60
gataaccgta tagagtcaga aggagggctc attgagacat ggaaccctaa caacaagcca    120
ttccagtgtg ccggtgttgc cctctctcgc tgcaccctca accgcaacgc ccttcgtag    179

SEQ ID NO: 25           moltype = DNA   length = 211
FEATURE                 Location/Qualifiers
source                  1..211
                        mol_type = genomic DNA
                        organism = Solanum tuberosum
SEQUENCE: 25
ccaattggta agtttctgct tctacctttg atatatatat aataattatc attaattagt     60
agtaatataa tatttcaaat atttttttca aaataaaaga atgtagtata tagcaattgc    120
ttttctgtat tttataagtg tgtatatttt aatttataac ttttctaata tatgaccaaa    180
atttgttgat gtgcagttgg gaaattgggt t                                   211

SEQ ID NO: 26           moltype = DNA   length = 57
FEATURE                 Location/Qualifiers
source                  1..57
                        mol_type = other DNA
                        organism = synthetic construct
misc_feature            1..57
                        note = Codon optimized
SEQUENCE: 26
atggctaagt tggttttttc tctctgtttt ttgctctttt ccggctgttg ctttgca        57

SEQ ID NO: 27           moltype = DNA   length = 63
FEATURE                 Location/Qualifiers
source                  1..63
                        mol_type = genomic DNA
                        organism = Arabidopsis thaliana
SEQUENCE: 27
atggactcta aaagtttcct cctgctgttg ctccttttt  gcttctattt tttgcacgac     60
gca                                                                   63

SEQ ID NO: 28           moltype = DNA   length = 221
FEATURE                 Location/Qualifiers
source                  1..221
                        mol_type = genomic DNA
                        organism = Agrobacterium tumefaciens
SEQUENCE: 28
gaaccgcaac gttgaaggag ccactgagcc gcgggtttct ggagtttaat gagctaagca     60
catacgtcag aaaccattat tgcgcgttca aaagtcgcct aaggtcacta tcagctagca    120
aatatttctt gtcaaaaatg ctccactgac gttccataaa ttcccctcgg tatccaatta    180
gagtctcata ttcactctca actcgatcga ggggatctac c                        221

SEQ ID NO: 29           moltype = DNA   length = 403
FEATURE                 Location/Qualifiers
source                  1..403
                        mol_type = genomic DNA
                        organism = Cauliflower mosaic virus
SEQUENCE: 29
tgagactttt caacaaagga taatttcggg aaacctcctc ggattccatt gcccagctat     60
ctgtcacttc atcgaaagga cagtagaaaa ggaaggtggc tcctacaaat gccatcattg    120
cgataaagga aaggctatca ttcaagatct ctctgccgac agtggtccca agatggacc     180
cccacccacg aggagcatcg tggaaaaaga agaggttcca accacgtcta caaagcaagt    240
ggattgatgt gacatctcca ctgacgtaag ggatgacgca caatcccact atccttcgca    300
agacccttcc tctatataag gaagttcatt tcatttggag aggacaacaa ttaccaacaa    360
caacaaacaa caaacaacat tacaattact atttacaatt aca                      403
```

| SEQ ID NO: 30 | moltype = DNA length = 1014 |
| --- | --- |
| FEATURE | Location/Qualifiers |
| source | 1..1014 |
| | mol_type = genomic DNA |
| | organism = Glycine max |

SEQUENCE: 30

```
atcagaatta aactttaatt ctagttaatt agaaaatttt aggtttaaat acaacttcag    60
tgatcttatt ttatttattc tgtaattta gtctctttat tttgaaataa aaattttgat   120
ccttcaattt taaaaaattc acaattaatt ttgatttcat tttcaattt gtcatttatt   180
tattttattt cttatatttt aattgaacaa ataatttatt gatgacactt taaatgaatt   240
ttttaggttt aagattaagt taaattaaaa taaaagcat aaaacataaa taaaattgag   300
aactaaaacta aaattatatt ttttaaaata aaaaaatctc tatttctgaa ataggtgaac   360
taaaattacc aatagaaaaa aataattaaa tgataaactt ttgaataatc tcactaatca   420
cttttaagat ctcttattca ataaattttt cttttacatt catagaactc atatccgaaa   480
cctaaggacc gaatcaatac cactcgatat gttgataaat aataattatt ttaaaatcta   540
aatctagtta aaataatttt tatttggttg aaaatgttaa tatctttata aaagtacagt   600
attacaagaa caaaatgaga aagaaattga aattcagtct aatttataaa taatcaacct   660
gcatgtaaaa ggaaagaaag aagcgagcag gaagaaaaga aatgaaacca tgcatggtcc   720
ccccacccc aggacatcat gggtttctgc catttgcaat acaaacactg aaacacctt   780
ctctttgtca cgtaatcgag attccgaagc caccttacac cattaactta atgaggtgta   840
agacagaagg gttccatagc catgcatact gaagaatgtc ttaagctcag cacccactt   900
ctgagacgtg tccctcattc accttcctct ctttccctata aataaccacg cctcaggttc   960
tccgcttcac aacacaaaca ttctctcat tgtccttga atataatact cagc           1014
```

| SEQ ID NO: 31 | moltype = DNA length = 403 |
| --- | --- |
| FEATURE | Location/Qualifiers |
| source | 1..403 |
| | mol_type = genomic DNA |
| | organism = Cauliflower mosaic virus |

SEQUENCE: 31

```
tgagactttt caacaaagga taatttcggg aaacctcctc ggattccatt gcccagctat    60
ctgtcacttc atcgaaagga cagtagaaaa ggaaggtggc tcctacaaat gccatcattg   120
cgataaagga aaggctatca ttcaagatct ctctgccgac agtggtccca agatggacc   180
cccaccacg aggagcatcg tggaaaaaga agaggttcca accacgtcta caaagcaagt   240
ggattgatgt gacatctcca ctgacgtaag ggatgacgca caatcccact atccttcgca   300
agaccctc tctatataag gaagttcatt tcatttggag aggacaacaa ttaccaacaa   360
caacaaacaa caaacaacat tacaattact atttacaatt aca                     403
```

| SEQ ID NO: 32 | moltype = DNA length = 382 |
| --- | --- |
| FEATURE | Location/Qualifiers |
| source | 1..382 |
| | mol_type = genomic DNA |
| | organism = Agrobacterium tumefaciens |

SEQUENCE: 32

```
ttttcaaatc agtgcgcaag acgtgacgta agtatccgag tcagttttta tttttctact    60
aatttggtcg tttatttcgg cgtgtaggac atggcaaccg ggcctgaatt tcgcgggtat   120
tctgtttcta ttcaactttt ttcttgatcc gcagccatta acgactttg aatagatacg   180
ctgacacgcc aagcctcgct agtcaaaagt gtaccaaaca acgctttaca gcaagaacgg   240
aatgcgcgtg acgctcgcgg tgacgccatt tcgcctttc agaaatggat aaatagcctt   300
gcttccatt atatcttccc aaaattaccaa tacattacac tagcatctga atttcataac   360
caatctcgat acaccaaatc ga                                            382
```

| SEQ ID NO: 33 | moltype = DNA length = 720 |
| --- | --- |
| FEATURE | Location/Qualifiers |
| source | 1..720 |
| | mol_type = other DNA |
| | organism = synthetic construct |
| misc_feature | 1..720 |
| | note = Original GFP sequence was from jellyfish. This has changes that increase the fluorescence of the protein as well as codon optimizations for expression in plants. |

SEQUENCE: 33

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcagcta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgcgggatc actcacggca tggacgagct gtacaagtaa   720
```

| SEQ ID NO: 34 | moltype = DNA length = 552 |
| --- | --- |
| FEATURE | Location/Qualifiers |
| source | 1..552 |
| | mol_type = other DNA |

```
                          organism = synthetic construct
misc_feature              1..552
                          note = Codon optimized
SEQUENCE: 34
atgagcccag aacgacgccc ggccgacatc cgccgtgcca ccgaggcgga catgccggcg    60
gtctgcacca tcgtcaacca ctacatcgag acaagcacgg tcaacttccg taccgagccg   120
caggaaccgc aggagtggac ggacgacctc gtccgtctgc gggagcgcta tccctggctc   180
gtcgccgagg tggacggcga ggtcgccggc atcgcctacg cgggtccctg gaaggcacgc   240
aacgcctacg actggacggc cgagtcgacc gtgtacgtct cccccgcca ccagcggacg    300
ggactgggct ccacgctcta cacccacctg ctgaagtccc tggaggcaca gggcttcaag   360
agcgtggtcg ctgtcatcgg gctgcccaac gacccgagcg tgcgcatgca cgaggcgctc   420
ggatatgccc cccgcggcat gctgcgggcg gccggcttca agcacgggaa ctggcatgac   480
gtgggttct ggcagctgga cttcagcctg ccggtgccgc cccgtccggt cctgcccgtc    540
accgaaatct ga                                                       552

SEQ ID NO: 35            moltype = DNA  length = 253
FEATURE                  Location/Qualifiers
source                   1..253
                         mol_type = genomic DNA
                         organism = Agrobacterium tumefaciens
SEQUENCE: 35
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg ggtttttatg attagagtcc cgcaattata catttaatac   180
gcgatagaaa acaaaatata gcgcgcaaac taggataaat tatcgcgcgc ggtgtcatct   240
atgttactag atc                                                      253
```

RECOMBINANT MICELLE AND METHOD OF IN VIVO ASSEMBLY

CROSS REFERENCE TO RELATED APPLICATIONS

This application is a continuation of U.S. application Ser. No. 18/075,250, filed Dec. 5, 2022, which is a continuation of U.S. application Ser. No. 17/717,000, filed Apr. 8, 2022, now U.S. Pat. No. 11,718,856, issued on Aug. 8, 2023, which is a continuation of U.S. application Ser. No. 16/741,680, filed Jan. 13, 2020, now U.S. Pat. No. 11,326,176, issued on May 10, 2022, which claims the benefit of U.S. Provisional Patent Application No. 62/939,247, filed Nov. 22, 2019, all of which are incorporated herein by reference in their entireties.

REFERENCE TO A SEQUENCE LISTING SUBMITTED VIA EFS-WEB

The instant application contains a Sequence Listing which has been submitted electronically in XML format and is hereby incorporated by reference in its entirety. Said XML format copy, created on Aug. 24, 2023, is named 62162-701_303 SL.xml and is 56,793 bytes in size.

TECHNICAL FIELD

An embodiment of the present disclosure relates generally to a micelle and more particularly to recombinant micelle and method of in vivo assembly in a plant cell.

BACKGROUND

Casein micelles account for more than 80% of the protein in bovine milk and are a key component of all dairy cheeses. Casein micelles include individual casein proteins are produced in the mammary glands of bovines and other ruminants. The industrial scale production of the milk that is processed to yield these casein micelles, primarily in the form of curds for cheese production, typically occurs on large-scale dairy farms and is often inefficient, damaging to the environment, and harmful to the animals. Dairy cows contribute substantially to greenhouse gasses, consume significantly more water than the milk they produce, and commonly suffer from dehorning, disbudding, mastitis, routine forced insemination, and bobby calf slaughter.

Accordingly, there is a need for an in vivo plant-based casein expression system which allows for purification of biologically active casein proteins that is cost effective at industrial scale.

Solutions to these problems have been long sought but prior developments have not taught or suggested any solutions and, thus, solutions to these problems have long eluded those skilled in the art.

DISCLOSURE OF INVENTION

An embodiment of the present invention provides a method of in vivo assembly of a recombinant micelle including: introducing a plasmid into a plant cell, wherein: the plasmid includes a segment of deoxyribonucleic acid (DNA) for encoding a ribonucleic acid (RNA) for a protein in a casein micelle, the segment of DNA is transcribed and translated; forming recombinant casein proteins in the plant cell, wherein: the recombinant casein proteins include a κ-casein and at least one of an $\alpha S_1$-casein, an $\alpha S_2$-casein, a β-casein; and assembling in vivo a recombinant micelle within the plant cell, wherein: an outer layer of the recombinant micelle is enriched with the κ-casein, an inner matrix of the recombinant micelle include at least one of the $\alpha S_1$-casein, the $\alpha S_2$-casein, the β-casein.

An embodiment of the present invention provides a recombinant micelle including: an outer layer enriched with a κ-casein; and an inner matrix including at least one of a $\alpha S_1$-casein, a $\alpha S_2$-casein, a β-casein.

An embodiment of the present invention provides a plasmid including a segment of deoxyribonucleic acid (DNA) for encoding a protein in a casein micelle wherein the segment of DNA includes a promoter and a N-terminal signal peptide.

Certain embodiments of the disclosure have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

FIG. 6 is an example of a schematic illustration of a portion of a plasmid in soybean.

FIG. 7 is an example of a schematic illustration of a portion of a plasmid in soybean for herbicide resistance in plants.

DETAILED DESCRIPTION

Figure 1:
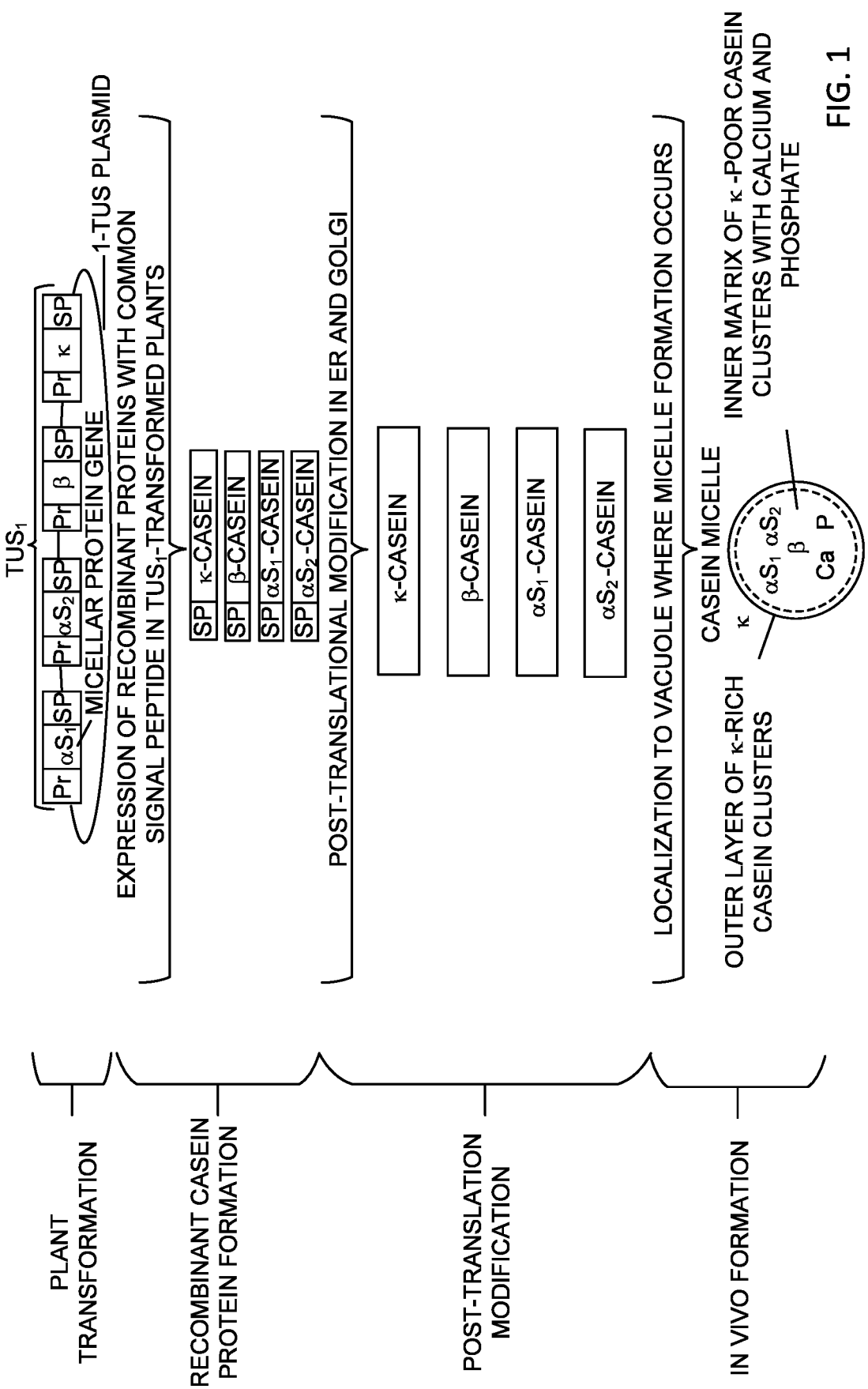
FIG. 1 is an example of a flow for forming in vivo casein micelles in an embodiment.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present disclosure.

In the following description, numerous specific details are given to provide a thorough understanding of the invention. However, it will be apparent that the invention may be practiced without these specific details. In order to avoid obscuring an embodiment of the present disclosure, some well-known techniques, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation.

The term "invention" or "present invention" as used herein is not meant to be limiting to any one specific embodiment of the invention but applies generally to any and all embodiments of the invention as described in the claims and specification.

Referring now to FIG. 1, therein is shown an example of a flow for forming in vivo casein micelles in an embodiment. In this example, FIG. 1 depicts the flow for forming the casein micelles by a plant transformation, a recombinant casein protein formation, a post-translation modification, and an in-vivo formation. As a specific example, FIG. 1 is a schematic illustration of the elements of a plasmid of this embodiment and its use in creation of micelles in vivo in a plant cell.

In this example for the plant transformation, a plant is transformed using a plasmid including a single transcription unit set. As used herein "plasmid" is a deoxyribonucleic acid (DNA) molecule capable of replication in a host cell and to which another DNA segment can be operatively linked so as to bring about replication of the attached DNA segment. As it relates to this example, methods for plant transformation include microprojectile bombardment as illustrated in U.S. Pat. Nos. 5,015,580; 5,550,318; 5,538,880; 6,153,812; 6,160,208; 6,288,312 and 6,399,861, all of which are incorporated herein by reference. Methods for plant transformation also include *Agrobacterium*-mediated transformation as illustrated in U.S. Pat. Nos. 5,159,135; 5,824,877; 5,591,616 and 6,384,301, all of which are incorporated herein by reference. Recipient cells for the plant transformation include, but are not limited to, meristem cells, callus, immature embryos, hypocotyls explants, cotyledon explants, leaf explants, and gametic cells such as microspores, pollen, sperm and egg cells, and any cell from which a fertile plant may be regenerated, as described in U.S. Pat. Nos. 6,194,636; 6,232,526; 6,541,682 and 6,603,061 and U.S. Patent Application publication US 2004/0216189 A1, all of which are incorporated herein by reference.

Continuing this example for the plant transformation, the plasmid including the single transcription unit set is shown and abbreviated in FIG. 1 as 1-TUS PLASMID. The transcription unit set included on this plasmid is transcription unit set 1 shown and abbreviated in FIG. 1 as $TUS_1$. As used herein "transcription unit set" is a segment of DNA including one or more transcription units. The purpose of a transcription unit set includes but is not limited to protein expression, gene suppression, regulatory ribonucleic acid (RNA) production, and herbicide resistance. As used herein "transcription unit" is a segment of DNA including at least a promoter DNA and transcribable DNA. As used herein "promoter" means regulatory DNA for initiating RNA transcription. A "plant promoter" is a promoter capable of initiating transcription in plant cells whether or not its origin is a plant cell. As used herein "terminator" means any DNA sequence that causes RNA transcription to terminate.

Further continuing this example for the plant transformation shown in FIG. 1 as an embodiment, the transcription unit set 1 includes four segments of DNA; each encoding RNA for one of the four proteins found in a casein micelle: an $\alpha S_1$ casein, an $\alpha S_2$ casein, a $\beta$ casein, and a $\kappa$ casein. For clarity and as an example, the genes encoding the $\alpha S_1$ casein, the $\alpha S_2$ casein, the $\beta$ casein, and the $\kappa$ casein are shown and abbreviated in FIG. 1 as $\alpha S_1$, as $\alpha S_2$, as $\beta$, and as $\kappa$, respectively, and shown and annotated in FIG. 1 as MICELLAR PROTEIN GENE. Each DNA segment encoding RNA for one of the four proteins found in a casein micelle is operably linked to a promoter, shown and abbreviated in FIG. 1 as P, and includes a plant-derived, tissue specific, N-terminal signal peptide, shown and abbreviated in FIG. 1 as SP. As used herein "operably linked" is the association of two or more DNA fragments in a DNA construct such that the function of one is controlled by the other, for example DNA encoding a protein associated with DNA encoding a promoter. In some embodiments, the N-terminal signal peptide targets the recombinant casein proteins to the plant vacuoles. In other embodiments, the recombinant casein proteins are targeted to and retained in the endoplasmic reticulum.

As an example for the recombinant casein protein formation, when the four segments of DNA included in transcription unit set 1 are transcribed and translated in a transgenic plant (not shown), four recombinant casein proteins, each including a plant-derived tissue specific signal peptide, are formed in the cytoplasm of the plant cell. The recombinant casein proteins are shown and abbreviated in FIG. 1 as $\alpha S_1$-CASEIN, as $\alpha S_2$-CASEIN, as $\beta$-CASEIN, and as $\kappa$-CASEIN, respectively, and are also referred to herein as "recombinant casein proteins" for brevity. As used herein, "transgenic" plant is a plant whose genome has been altered by the stable integration of recombinant DNA. As an example of stable integration, the transgenic plant includes a plant regenerated from an originally-transformed plant cell and progeny transgenic plants from later generations or crosses of a transformed plant. As used herein "recombinant DNA" refers to DNA which has been synthesized, assembled or constructed outside of a cell. Examples of recombinant DNA can include DNA containing naturally occurring DNA or complementary DNA (cDNA) or synthetic DNA.

As it relates to this example for the post-translation modification shown in FIG. 1 as an embodiment, the four recombinant casein proteins in the cytoplasm of the plant cell include the $\alpha S_1$-casein, the $\alpha S_2$-casein, the $\beta$-casein, and the $\kappa$-casein, each including a signal peptide (SP) that localizes the recombinant casein protein to specific organelles, for example the secretory pathway and protein storage vacuoles, in the plant cell. The signal peptide is removed from the recombinant casein proteins during post-translational modification that occurs in the endoplasmic reticulum and the Golgi apparatus of the plant cell. For clarity in this example, the endoplasmic reticulum and the Golgi apparatus are shown and abbreviated in FIG. 1 as ER, and as GOLGI, respectively. In this embodiment and example, phosphorylation occurs on the recombinant casein proteins prior to, during, or after migration to a specific tissue, shown in FIG. 1 as circles enclosing the letter "P" attached to each of the recombinant casein proteins. In other embodiments and examples, one or more post-translational modifications of the recombinant casein proteins can occur, including phosphorylation, glycosylation, ubiquitination, nitrosylation, methylation, acetylation, lipidation and proteolysis. In other embodiments no post-translational modifications occur on the recombinant casein proteins, or in other words, the post-translation modification is optional.

Continuing this example for the in vivo formation as an embodiment, an outer layer of the micelle is enriched in recombinant κ-casein shown and abbreviated in FIG. 1 as κ, and an inner matrix of the micelle includes the recombinant $αS_1$-casein, the recombinant $αS_2$-casein, the recombinant β-casein, the calcium and the phosphate, shown in and annotated in FIG. 1 as $αS_1$, $αS_2$, as αS, and β, respectively. Micelle formation is enhanced by the presence of intracellular calcium and phosphate, shown and abbreviated in FIG. 1 as Ca and P, respectively.

Figure 2:
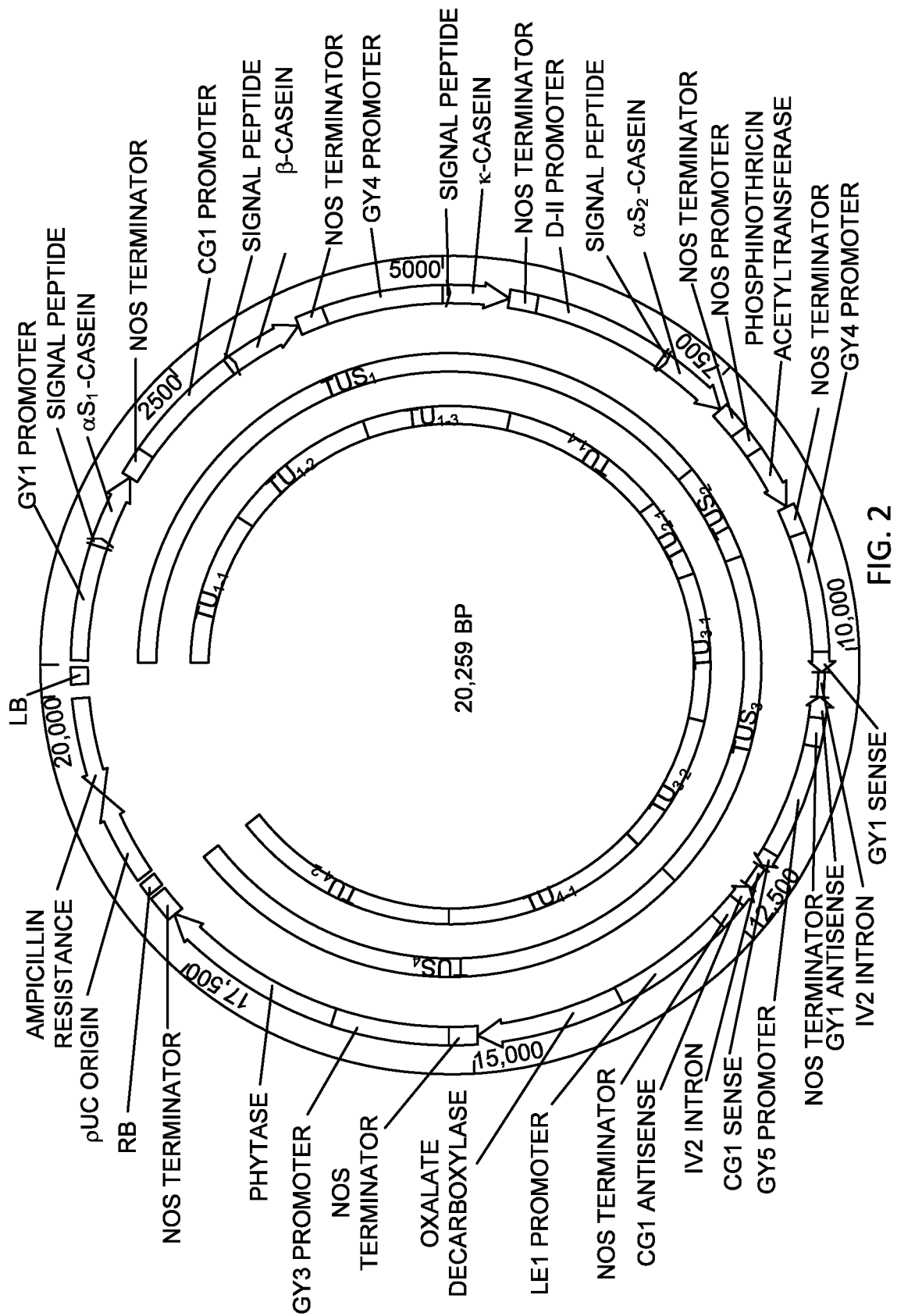
FIG. 2 is an example of a schematic illustration of a plasmid used in FIG. 1.

Referring now to FIG. 2, therein is shown an example of a schematic illustration of a plasmid used in FIG. 1. As a specific example, FIG. 2 is a schematic illustration of the elements of a plasmid of this embodiment.

In this example for the plant transformation of FIG. 1, an embodiment provides a plant that is transformed with one or more transfer DNAs including one or more transcription unit sets. As used herein "transfer DNA" (T-DNA) is DNA which integrates or is integrated into a genome.

For example, an *Agrobacterium*-mediated transformation T-DNA is part of a binary plasmid, which is flanked by T-DNA borders, and the binary plasmid is transferred into an *Agrobacterium tumefaciens* strain carrying a disarmed tumor inducing plasmid. Also for example, for a biolistic mediated transformation a gene gun is used for delivery of T-DNA, which is typically a biolistic construct containing promoter and terminator sequences, reporter genes, and border sequences or signaling peptides, to cells.

Continuing the example of a T-DNA used to transform a plant in an embodiment, the T-DNA includes four transcription unit sets: a transcription unit set 1, a transcription unit set 2, a transcription unit set 3, and a transcription unit set 4. For clarity, the transcription unit set 1, the transcription unit set 2, the transcription unit set 3, and the transcription unit set 4 are shown and abbreviated in FIG. 2 as $TUS_1$, as $TUS_2$, as $TUS_3$, and as $TUS_4$, respectively.

In this example as an embodiment, $TUS_1$ includes one transcription unit for each of the four casein proteins found in a casein micelle of FIG. 2: a transcription unit 1-1 includes DNA encoding $αS_1$-casein, a transcription unit 1-2 includes DNA encoding β-casein, a transcription unit 1-3 includes DNA encoding κ-casein, and a transcription unit 1-4 includes DNA encoding $αS_1$-casein. For clarity and brevity, the transcription unit 1-1, the transcription unit 1-2, the transcription unit 1-3, and the transcription unit 1-4 are shown and abbreviated in FIG. 2 as $TU_{1-1}$, as $TU_{1-2}$, as $TU_{1-3}$, and as $TU_{1-4}$, respectively. Each transcription unit in $TUS_1$ can also include DNA encoding the same plant-derived signal peptide. Additionally, each transcription unit in $TUS_1$ includes a promoter and a transcriptional terminator.

Continuing this example as an embodiment, $TUS_2$ includes one transcription unit, shown and abbreviated in FIG. 2 as $TU_{2-1}$, that includes a promoter, DNA encoding phosphinothricin acetyltransferase, and a transcriptional terminator. In other embodiments, $TUS_2$ can include one or more genes encoding a selectable marker that can impart herbicide or antibiotic resistance which enables the selection of transformed plants that produce micelles in vivo. Genes enabling selection of transformed plants include those conferring resistance to antibiotics, including as examples kanamycin, hygromycin B, gentamicin, and bleomycin. Genes enabling selection of transformed plants also include those conferring resistance to herbicides, including as examples a glyphosate herbicide, a phosphinothricin herbicide, an oxynil herbicide, an imidazolinone herbicide, a dinitroaniline herbicide, a pyridine herbicide, a sulfonylurea herbicide, a bialaphos herbicide, a sulfonamide herbicide, and a glufosinate herbicide. Examples of such selectable markers are illustrated in U.S. Pat. Nos. 5,550,318; 5,633,435; 5,780,708 and 6,118,047, all of which are incorporated herein by reference. In other embodiments, $TUS_2$ includes one or more genes expressing a screenable marker which enables the visual identification of transformed plants that produce micelles in vivo. Genes expressing a screenable marker include genes encoding a colored or fluorescent protein, including as examples luciferase or green fluorescent protein (U.S. Pat. No. 5,491,084, herein incorporated by reference), and genes expressing β-glucuronidase or uidA gene (U.S. Pat. No. 5,599,670, herein incorporated by reference) for which various chromogenic substrates are known. In some embodiments, each of the genes encoding a selectable or screenable marker are operably linked to an inducible promoter, such as for example a NOS promoter, or a tissue-specific promoter, such as for example a promoter from the soybean a' subunit of β-conglycinin, such that the translation of the selectable or screenable markers can be regulated.

Continuing this example as an embodiment, $TUS_3$ includes two transcription units that yield untranslated RNA molecules that suppress native seed protein gene translation. The first transcription unit in $TUS_3$, a transcription unit 3-1, includes the sense strand, or coding strand, of DNA encoding soybean Glycinin1, and the antisense strand, or non-coding strand, of DNA encoding soybean Glycinin1 separated by the potato IV2 intron. For clarity and brevity, the transcription unit 3-1 the sense strand or coding strand of DNA encoding soybean Glycinin1, and the antisense strand or non-coding strand of DNA encoding soybean Glycinin1, the potato IV2 intron are shown and annotated in FIG. 2 as $TU_{3-1}$ as GY1 SENSE, as GY1 ANTISENSE, and as IV2 INTRON, respectively. The second transcription unit in $TUS_3$, a transcription unit 3-2 includes the sense strand, or coding strand, of DNA encoding β-conglycinin 1 and the antisense strand, or non-coding strand, of DNA encoding β-conglycinin 1 separated by the potato IV2 intron. For clarity and brevity, the transcription unit 3-2, the sense strand or coding strand of DNA encoding β-conglycinin 1, the antisense strand or non-coding strand of DNA encoding β-conglycinin 1, and the potato IV2 intron are shown and annotated in FIG. 2 as $TU_{3-2}$ as CG1 SENSE, as CG1 ANTISENSE, and as IV2 INTRON, respectively.

In other embodiments, $TUS_3$ includes other transcription units that yield untranslated RNA molecules that suppress native seed protein gene translation. As an example, in other embodiments, $TUS_3$ includes one transcription unit, a transcription unit 3-1, that includes a promoter from the soybean GY4 gene (SEQ ID NO:15), a miR319a microRNA from *Arabidopsis thaliana* that has been modified such that the homologous arms of the microRNA hairpin contain 21 nucleotide sequences matching a portion of the soybean GY1 gene sequence (SEQ ID NO:10), and a NOS transcriptional terminator (SEQ ID NO:35) (not shown).

Continuing this example as an embodiment, $TUS_4$ includes two transcription units that encode proteins which alter the intracellular environment in a manner that optimizes the production of micelles having requisite attributes including size, mineral content, protein content, protein distribution, and mass. The first transcription unit in $TUS_4$, a transcription unit 4-1 includes a promoter, DNA encoding oxalate decarboxylase, and a transcriptional terminator. For clarity and brevity, the transcription unit 4-1 is shown and abbreviated in FIG. 2 as $TU_{4-1}$. The second transcription unit in $TUS_4$, a transcription unit 4-2, includes a promoter, DNA encoding phytase, and a transcriptional terminator. For clarity and brevity, the transcription unit 4-2 is shown and abbreviated as $TU_{4-2}$. In this embodiment, transcription and translation of $TU_{4-1}$ yields an oxalate-degrading enzyme which increases the amount of free intracellular calcium available for capture and inclusion during micelle formation. Also in this embodiment, transcription and translation of $TU_{4-2}$ yields a phytase enzyme which increases the amount of free intracellular phosphate available for capture and inclusion during micelle formation. In some embodiments, each of the genes encoding oxalate-degrading enzymes or phytase enzymes are operably linked to a constitutive promoter, tissue specific promoter or an inducible promoter, such as for example, a nopaline synthase promoter or a promoter from the soybean β-conglycinin gene, such that the translation of proteins which alter the intracellular environment can be regulated. In some embodiments, $TUS_4$ includes both a transcription unit 4-1 that increases the intracellular calcium concentration and a transcription unit 4-2 that increases the intracellular phosphate concentration. In other embodiments, $TUS_4$ includes only a transcription unit 4-1 that increases the intracellular calcium concentration. In other embodiments, $TUS_4$ includes only a transcription unit 4-2 that increases the intracellular phosphate concentration.

In other embodiments, $TUS_4$ includes transcription units that increase the intracellular calcium concentration by expressing an oxalate oxidase enzyme (not shown). As an example, in other embodiments, $TUS_4$ includes one transcription unit, a transcription unit 4-1, that includes a promoter from the soybean GY4 gene (SEQ ID NO:15), the coding sequence for the oxalate oxidase 1 coding sequence from wheat that has been codon optimized for expression in soybean (SEQ ID NO:9), and the NOS transcriptional terminator (SEQ ID NO:35) (not shown). In other embodiments, $TUS_4$ includes transcription units that increase the intracellular phosphate concentration by suppressing the expression of the soybean myo-inositol-3-phosphate synthase (MIPS1) gene. As an example, in other embodiments, $TUS_4$ includes one transcription unit, a transcription unit 4-2, that includes a promoter from the soybean GY4 gene (SEQ ID NO:15), a portion of the MIPS1 coding sequence lacking a start codon (SEQ ID NO:21), the IV2 intron from potato (SEQ ID NO:25), the antisense of the MIPS1 sequence (SEQ ID NO:22), and the NOS transcriptional terminator (SEQ ID NO:35) (not shown).

In some embodiments of the disclosure, transcription unit sets are assembled in numeric order. In other embodiments, transcription unit sets can be assembled in any order.

In some embodiments of the disclosure, the plant is transformed with a plasmid that contains transcription unit sets $TUS_1$, $TUS_2$, $TUS_3$, and $TUS_4$. In other embodiments of the disclosure, the plant is transformed with a plasmid that contains only transcription unit set $TUS_1$.

In some embodiments of the disclosure, the plant is transformed with a plasmid that contains transcription unit sets $TUS_1$, and $TUS_2$. In other embodiments of the disclosure, the plant is transformed with a plasmid that contains transcription unit sets $TUS_1$, $TUS_2$, and $TUS_3$. In other embodiments of the disclosure, the plant is transformed with a plasmid that contains transcription unit sets $TUS_1$, $TUS_2$, and $TUS_4$.

In other embodiments of the disclosure, the plant is transformed with a plasmid that contains transcription unit sets $TUS_1$, and $TUS_3$. In other embodiments of the disclosure, the plant is transformed with a plasmid that contains transcription unit sets $TUS_1$, $TUS_3$, and $TUS_4$.

In other embodiments of the disclosure, the plant is transformed with a plasmid that contains transcription unit sets $TUS_1$, and $TUS_4$. In some embodiments of the disclosure, transgenic plants are prepared by crossing a first plant that has been transformed with a plasmid containing one or more transcription unit sets with a second untransformed plant. In other embodiments of the disclosure, transgenic plants are prepared by crossing a first plant that has been transformed with a plasmid containing one or more but not all transcription unit sets required for micelle formation in vivo with a second plant having one or more transcription unit sets, wherein at least one of the transcription unit sets is present in the second plant and not present in the first plant.

In some embodiments of the disclosure, transgenic plants are prepared by crossing a first plant that has been transformed with a plasmid containing one or more transcription unit sets enabling micelle formation in vivo with a second plant having another trait, such as herbicide resistance or pest resistance.

In some embodiments of the disclosure, transgenic plants are prepared by growing progeny generations of a plant that has been transformed with a plasmid containing one or more transcription unit sets enabling micelle formation in vivo. In other embodiments, transgenic plants are prepared by growing progeny generations of a transgenic plant produced by crossing one or more plants that have been transformed with a plasmid containing one or more transcription unit sets enabling micelle formation in vivo.

Further to this example shown in FIG. 2 as an embodiment, the promoters in the four transcription unit sets include the promoters of genes coding for soybean Glycinin1, soybean β-conglycinin1, soybean Glycinin4, soybean Bowman-Birk protease inhibitor, *Agrobacterium* nopaline synthase, soybean Glycinin5, soybean lectin, and soybean Glycinin3. For clarity and brevity, the promoters of genes coding for soybean Glycinin1 is shown and annotated in FIG. 2 as GY1 PROMOTER. Also for clarity and brevity, the soybean β-conglycinin1 is shown and annotated in FIG. 2 as CG1 promoter. Further for clarity and brevity, the soybean Glycinin4 is shown and annotated in FIG. 2 as GY4 promoter. Yet further for clarity and brevity, the Bowman-Birk protease inhibitor promoter is shown and annotated in FIG. 2 as D-II promoter. Yet further for clarity and brevity, the *Agrobacterium* nopaline synthase is shown and annotated in FIG. 2 as NOS promoter. Yet further for clarity and brevity, the soybean Glycinin5 is shown and annotated in FIG. 2 as GY5 promoter. Yet further for clarity and brevity, the soybean lectin is shown and annotated in FIG. 2 as LE1 promoter. Yet further for clarity and brevity, the soybean Glycinin3 is shown and annotated in FIG. 2 as GY3 promoter.

In other embodiments and examples, promoters in one or more of the four transcription unit sets include a promoter capable of initiating transcription in plant cells whether or not an origin of the promoter is a plant cell. For example,

*Agrobacterium* promoters are functional in plant cells. The promoters capable of initiating transcription in plant cells include promoters obtained from plants, plant viruses and bacteria such as *Agrobacterium*.

As specific examples of promoters under developmental control include promoters that preferentially initiate transcription in certain tissues, such as leaves, roots, or seeds. Such promoters are referred to as "tissue preferred". Also as specific examples of promoters that initiate transcription only in certain tissues are referred to as "tissue specific". Further as a specific example, a "cell type specific" promoter primarily drives expression in certain cell types in one or more organs, for example, vascular cells in roots or leaves. Yet further a specific example, an "inducible" or "repressible" promoter is a promoter which is under environmental control. Examples of environmental conditions that may affect transcription by inducible or repressible promoters include anaerobic conditions, or certain chemicals, or the presence of light. Tissue preferred, tissue specific, cell type specific, and inducible or repressible promoters constitute the class of "non-constitutive" promoters. A "constitutive" promoter is a promoter which is active under most conditions.

Returning to this example in FIG. 2 as an embodiment, the transcriptional terminators in the four transcription unit sets include the termination sequence of the nopaline synthase gene, shown and annotated in FIG. 2 as NOS terminator. In other embodiments, the transcriptional terminators in one or more of the four transcription unit sets includes transcriptional terminators from the native soybean Glycinin genes, or any other plant transcriptional terminators.

In this example as an embodiment, the T-DNA used to transform a plant also includes DNA encoding an origin of replication, a gene conferring antibiotic resistance, a right boundary for the T-DNA, and a left boundary for the T-DNA, shown and annotated in FIG. 2 as pUC origin, ampicillin resistance, RB, and LB, respectively. In this embodiment, the gene conferring antibiotic resistance is a gene conferring resistance to the antibiotic ampicillin. In other embodiments, the gene conferring antibiotic resistance is a gene conferring resistance to any other antibiotic, including kanamycin and chloramphenicol.

Figure 3A:
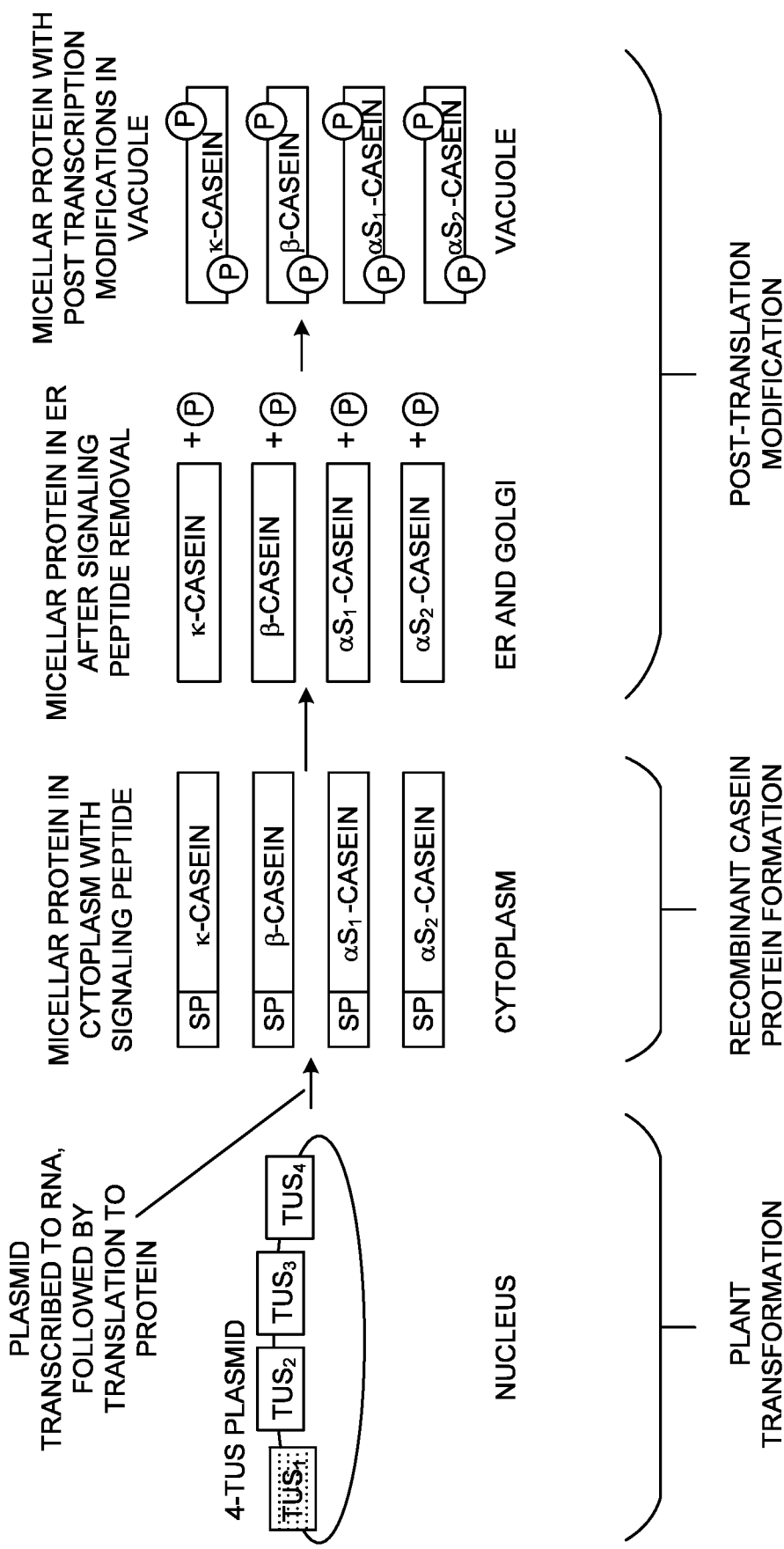
FIG. 3A is an example with additional details from the plant transformation to the post-translation modification.

Referring now to FIG. 3A, therein is shown an example with additional details from the plant transformation to the post-translation modification. The plant transformation and the post-translation modification are also described in FIG. 1. The example depicted in FIG. 3A also depicts the recombinant casein protein formation, also described in FIG. 1. As a specific example, FIG. 3A schematically illustrates the transcription of casein proteins from genes in $TUS_1$ as well as post transcriptional alterations that occur as the proteins move towards their subcellular specific destination encoded by the common signal peptide.

In the example shown in FIG. 3A, the purpose of transcription unit set 1 is forming casein micelles in vivo in an embodiment. In this example, the plant transformation depicts a plant transformed using a T-DNA including four transcription unit sets shown and annotated in FIG. 3A as 4-TUS plasmid. The T-DNA includes transcription unit set 1, shown and abbreviated in FIG. 3A as $TUS_1$, which includes one transcription unit for each of the four casein proteins found in a casein micelle, with each transcription unit including DNA encoding the same plant-derived signal peptide, a promoter and a transcriptional terminator as described in FIG. 2. Upon transcription and translation of $TUS_1$ in the transgenic plant during the recombinant casein protein formation, the four recombinant casein proteins ($\alpha S_1$-casein, $\alpha S_2$-casein, $\beta$-casein, and $\kappa$-casein) are formed in the cytoplasm, each including a signal peptide that localizes the recombinant protein to a specific tissue, for example the secretory pathway and protein storage vacuoles, in the plant cell. In this example, the signal peptide is removed from the recombinant casein proteins during post-translational modification that occurs in the endoplasmic reticulum, abbreviated as ER, of the plant cell.

Continuing this example and embodiment for the post-translation modification, phosphorylation occurs on the recombinant casein proteins prior to, during, or after migration to a specific tissue. The phosphorylation is shown in FIG. 3A as circles enclosing the letter "P" that are added to and then attached to each of the recombinant casein proteins to form phosphorylated casein proteins. The phosphorylated casein proteins are then localized to the vacuole where micelle assembly occurs in vivo. In some embodiments, proteins encoded by $TUS_2$ transcription units (not shown) are also phosphorylated, glycosylated, or a combination thereof. In other embodiments, the casein proteins encoded by $TUS_4$ transcription units (not shown) are also phosphorylated or glycosylated or both. In other embodiments, no post-translational modifications occur to proteins encoded by $TUS_1$, $TUS_2$, $TUS_3$, or $TUS_4$ (not shown). As another example and embodiment, a kinase gene may optionally be included to generate a kinase protein that ensures phosphorylation of the casein proteins encoded by $TUS_4$ transcription units (not shown).

Figure 3B:
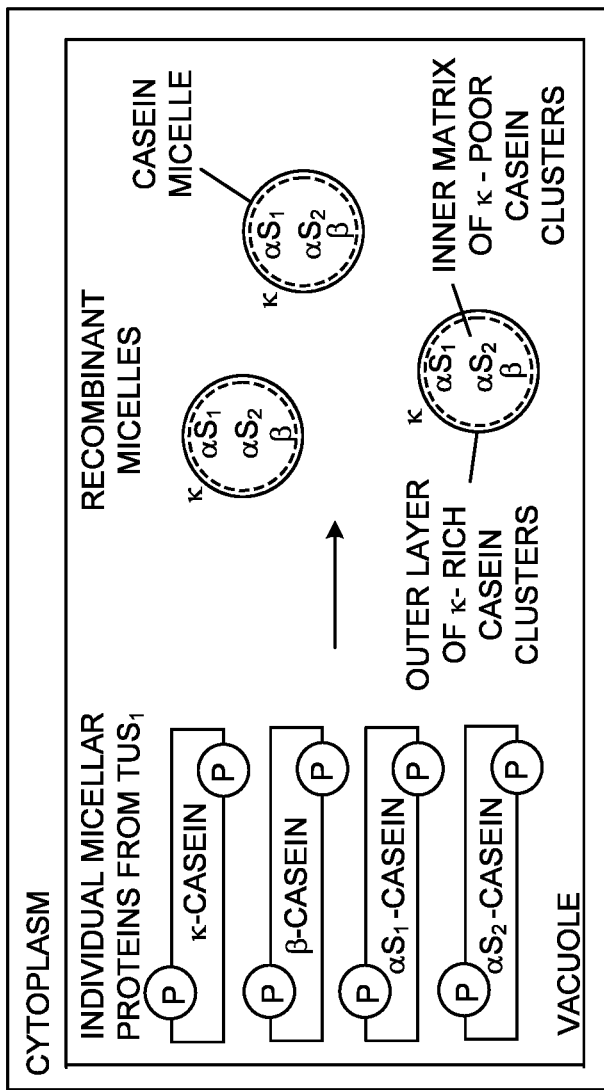
FIG. 3B is an example with additional details for the in vivo formation.

Referring now to FIG. 3B, therein is shown an example with additional details for the in vivo formation. The in vivo formation is also described in FIG. 1. As a specific example, FIG. 3B schematically illustrates the in vivo formation of recombinant micelles inside a plant cell.

Upon localization to the vacuole, each of the four recombinant casein proteins assemble with the other recombinant casein proteins to form micelles in vivo. In this example, the outer layer of the micelle is enriched in recombinant $\kappa$-casein shown and abbreviated in FIG. 3B as and the inner matrix of the micelle includes recombinant $\alpha S_1$-casein and $\alpha S_2$-casein, shown and abbreviated as $\alpha S_1$ and $\alpha S_2$, respectively, in FIG. 3B, and $\beta$-casein, shown and abbreviated in FIG. 3B as $\beta$.

Figure 3C:
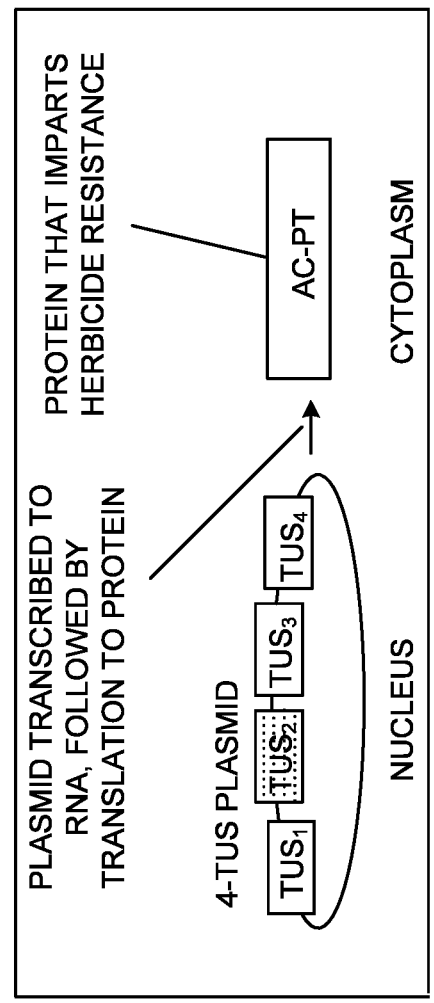
FIG. 3C is an example of a schematic illustration of a transcription of proteins which impart herbicide resistance to the transformed plant.

Referring now to FIG. 3C, therein is shown an example of a schematic illustration of a transcription of proteins which impart herbicide resistance to the transformed plant. FIG. 3C depicts an example of the purpose of transcription unit set 2 in an embodiment.

In this example, a plant is transformed using a T-DNA including four transcription unit sets shown and annotated in FIG. 3C as 4-TUS plasmid. The T-DNA includes transcription unit set 2, shown in FIG. 3C and abbreviated as $TUS_2$ which includes one transcription unit that includes DNA encoding phosphinothricin acetyltrasnferase that imparts herbicide resistance and allow for selection of transformed cells producing micelles, shown and abbreviated as AC-PT in FIG. 3C, and a promoter and a transcriptional terminator (not shown).

Figure 3E:
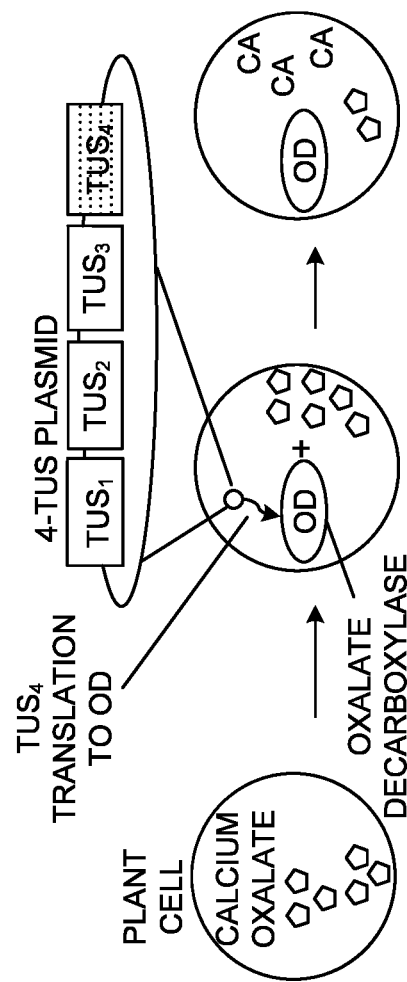
FIG. 3E is an example of a schematic illustration of a transcription of a portion of the plasmid of FIG. 1 and resulting proteins used to increase calcium concentrations in the plant cell.
Figure 3D:
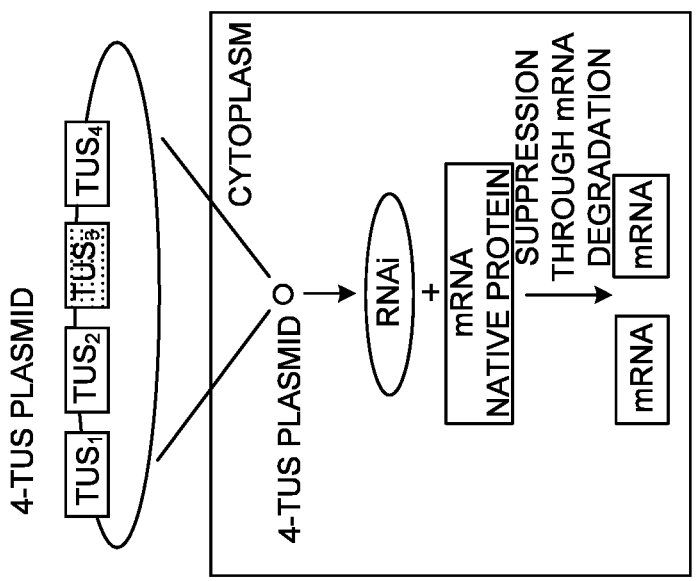
FIG. 3D is an example of a schematic illustration of suppression of native seed storage proteins by RNAi transcribed by a portion of the plasmid of FIG. 1.

Referring now to FIG. 3D, therein is shown an example of a schematic illustration of suppression of native seed storage proteins by interference RNA (RNAi) transcribed by a portion of the plasmid of FIG. 1. As a specific example, FIG. 3D schematically illustrates suppression of native seed storage proteins by RNAi transcribed by one or more genes in $TUS_3$.

FIG. 3D depicts an example of the purpose of transcription unit set 3 in an embodiment. In this example, a plant is transformed using a T-DNA including four transcription unit sets, shown and annotated in FIG. 3D as 4-TUS plasmid. The T-DNA includes transcription unit set 3, shown and abbreviated in FIG. 3D as $TUS_3$, which includes one or more transcription units that yield untranslated RNA molecules that suppress native seed protein gene translation thereby freeing cellular resources to produce micelles in vivo. Transcription of the DNA in $TUS_3$ yields RNAi, shown and abbreviated in FIG. 3D as RNAi, that targets messenger RNA of native plant proteins or native plant peptides, shown and annotated in FIG. 3D as mRNA NATIVE PROTEIN, and suppresses the expression of those messenger RNAs through messenger RNA degradation such that the recombinant casein proteins encoded by $TUS_1$, described in FIG. 1, FIG. 3A, and FIG. 3B, can be translated at higher quantities, thereby yielding higher concentrations of micelles in vivo (not shown). In some embodiments, DNA encoding RNAi is operably linked to a constitutive promoter or an inducible promoter (not shown), such as for example a nopaline synthase promoter or soybean α' subunit of β-conglycinin, such that the suppression of native seed protein gene translation by RNAi can be regulated.

Figure 3F:
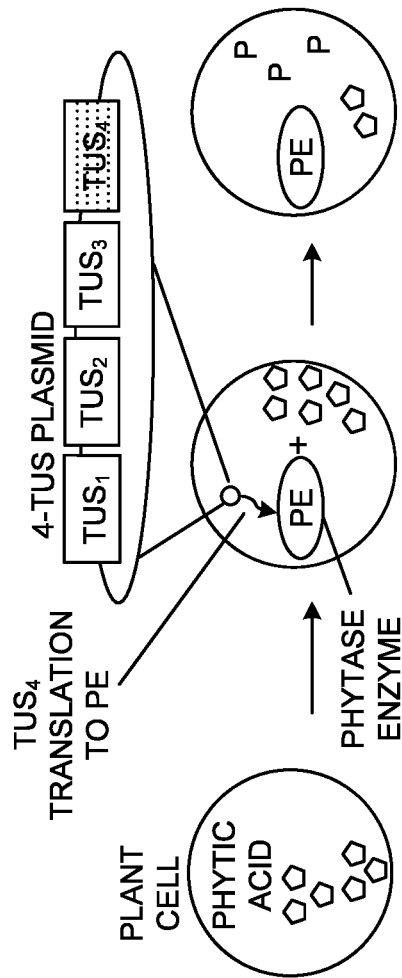
FIG. 3F is an example of a schematic illustration of a transcription of a portion of the plasmid of FIG. 1 and resulting proteins used to increase phosphate concentrations in the plant cell.

Referring now to FIG. 3E and FIG. 3F, therein are shown examples of schematic illustrations of a transcription of a portion of the plasmid of FIG. 1 and resulting proteins used to alter the intracellular conditions of the plant cell. As specific examples, FIG. 3E and FIG. 3F schematically illustrate the transcription of $TUS_4$ genes and the resulting proteins used to alter the conditions in the cytoplasm of the cell.

FIG. 3E depicts an example of the purpose of transcription unit set 4 in an embodiment. In this example, a plant is transformed using a T-DNA including four transcription unit sets, shown and annotated in FIG. 3E as 4-TUS plasmid. The T-DNA includes transcription unit set 4, shown and abbreviated in FIG. 3E as $TUS_4$, which includes one or more transcription units that encode proteins which increase the concentration of intracellular minerals, including calcium and phosphate. In this example, $TUS_4$ includes one transcription unit, a $TU_{4-1}$, that includes a promoter, DNA encoding oxalate decarboxylase, and a transcriptional terminator (not shown). Transcription and translation of $TU_{4-1}$ yields the enzyme oxalate decarboxylase, shown and abbreviated in FIG. 3E as OD, that breaks down the calcium oxalate and increases calcium levels in the plant cell. The increased intracellular calcium enhances the formation of recombinant casein micelles in the plant cell (not shown).

FIG. 3F depicts an example of the purpose of transcription unit set 4 in an embodiment. In this example, a plant is transformed using a T-DNA including four transcription unit sets, shown and annotated in FIG. 3F as 4-TUS plasmid. The T-DNA includes transcription unit set 4, shown and abbreviated in FIG. 3F as $TUS_4$, which includes one or more transcription units that encode proteins which increase the concentration of intracellular minerals, including calcium and phosphate. In this example, $TUS_4$ includes one transcription unit, a $TU_{4-2}$, that includes a promoter, DNA encoding a phytase enzyme, and a transcriptional terminator (not shown). Transcription and translation of $TU_{4-2}$ yields the phytase enzyme, shown and abbreviated in FIG. 3F as PE, that breaks down the phytic acid and increases phosphate levels in the plant cell. The increased intracellular phosphate enhances the formation of recombinant casein micelles in the plant cell (not shown).

Figure 3G:
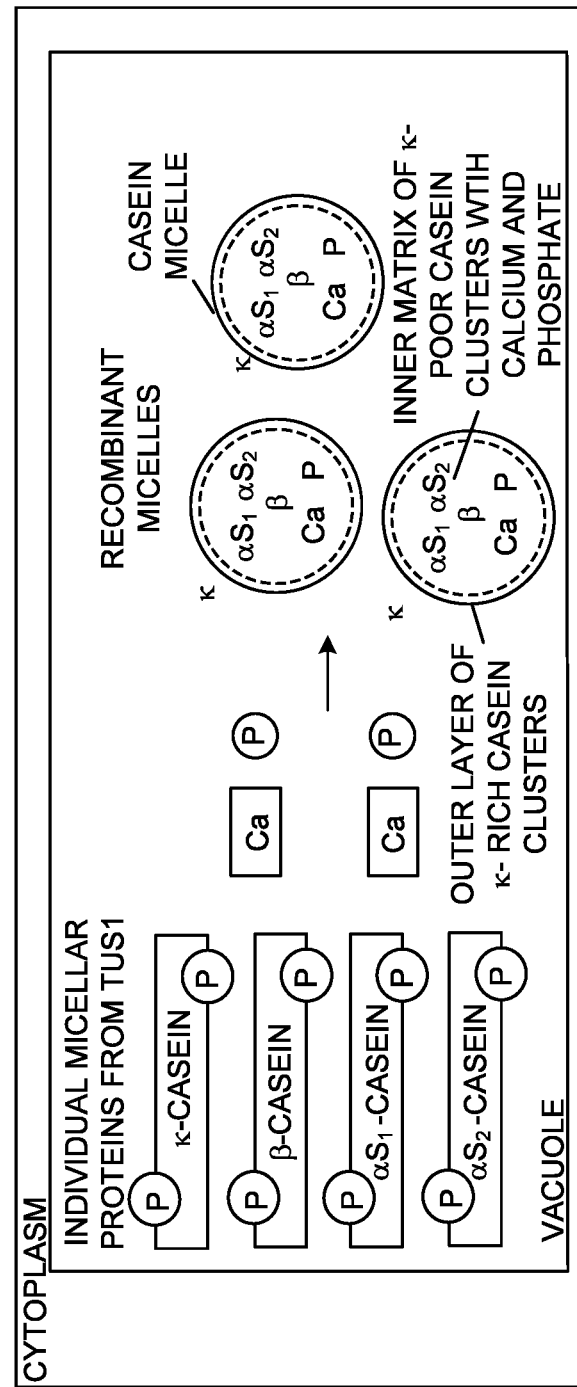
FIG. 3G is an example with further additional details of the in vivo formation.

Referring now to FIG. 3G, therein is shown an example of further additional details of the in vivo formation. The in vivo formation is also described in FIG. 1, FIG. 3A, and FIG. 3B. As a specific example, FIG. 3G schematically illustrates the in vivo formation of recombinant micelles inside a plant cell.

In the example shown in FIG. 3G, the in vivo formation of recombinant micelles inside a plant cell in which the four micellar proteins are produced by transcription and translation of transcription unit set 1 as depicted and described in FIG. 3A. The levels of calcium in plant cell vacuoles is increased by the presence of oxalate decarboxylase produced by transcription and translation of transcription unit set 4 as depicted and described in FIG. 3E. In this example, the four casein proteins encoded by transcription unit 1 are phosphorylated and localized to the plant cell vacuole where the intracellular calcium and the intracellular phosphate enhances the formation of recombinant casein micelles in the plant cell vacuole.

Figure 4:
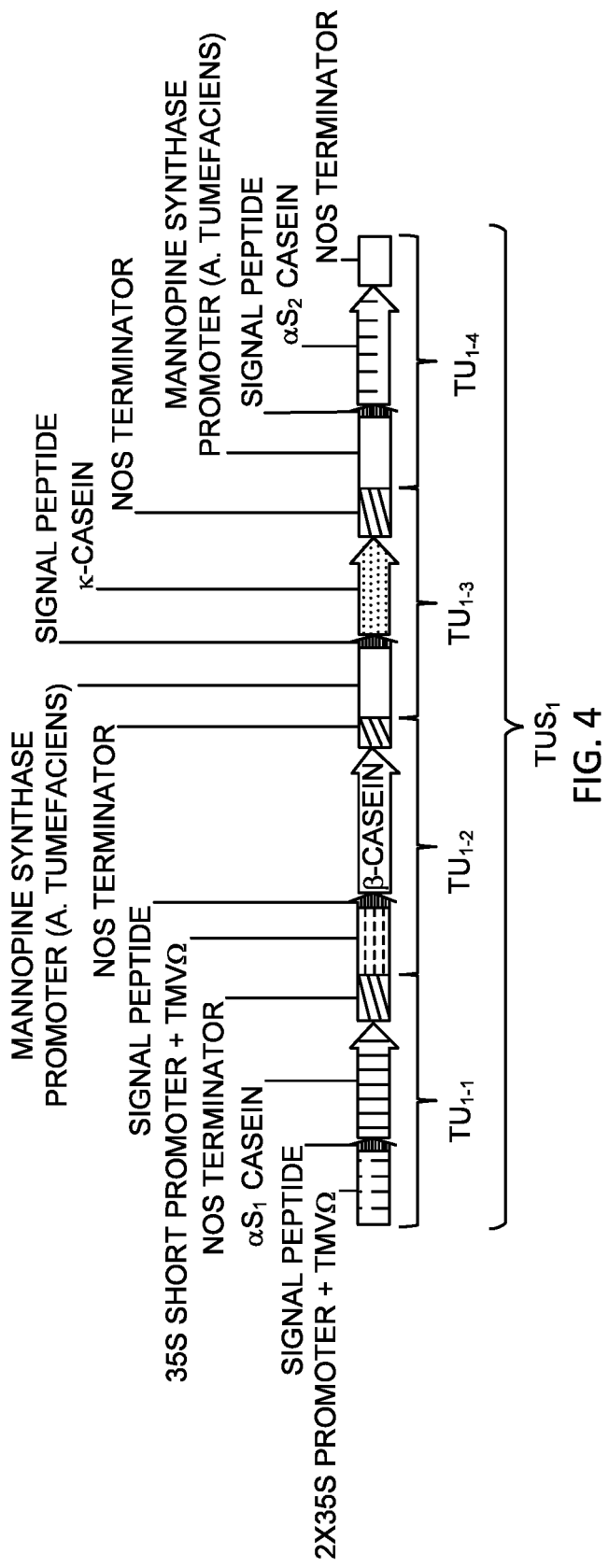
FIG. 4 is an example of a schematic illustration of a portion of a plasmid in Arabidopsis.
Figure 5:
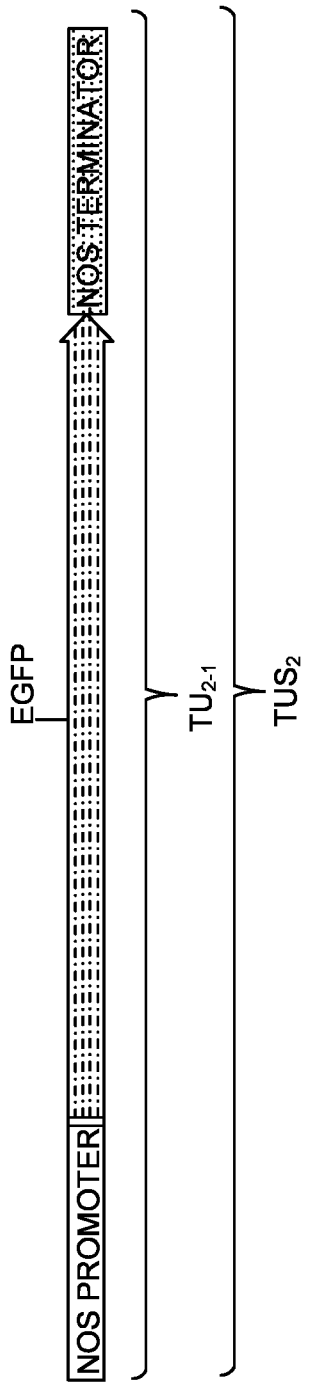
FIG. 5 is an example of a schematic illustration of a portion of a plasmid in Arabidopsis for a screenable marker in plants.

Aspects of the disclosure can be further illustrated by a specific embodiment in which a casein micelle is assembled in vivo from its constituent proteins in *Arabidopsis thaliana* as further described in FIG. 4 and FIG. 5.

Referring now to FIG. 4, therein is shown an example of a schematic illustration of a portion of a plasmid in Arabidopsis. The example shown in FIG. 4 is also described in FIG. 2. As a specific example, FIG. 4 schematically illustrates elements of plasmids that encode micellar component proteins. Transcription units depicted are components of $TUS_1$ in Arabidopsis.

The example in FIG. 4 depicts a transcription unit set which can be used for creation of casein micelles in vivo in *Arabidopsis thalian*. The transcription unit set includes one transcription unit for each of the four casein proteins found in a casein micelle, abbreviated and shown in FIGS. 4 as $TU_{1-1}$, $TU_{1-2}$, $TU_{1-3}$, and $TU_{1-4}$. The transcription unit set abbreviated and shown in FIG. 4 as $TUS_1$. Each of the four transcription units includes a promoter, a plant-derived N-terminal signal peptide, DNA encoding one of the four proteins found in a casein micelle, and a transcriptional terminator.

Continuing this example, $TU_{1-1}$ includes a double 35S promoter containing the tobacco mosaic virus omega leader sequence (SEQ ID NO:29), a signal peptide from the Arabidopsis CLV3 gene (SEQ ID NO:27), the $αS_1$-casein coding sequence codon optimized for expression in Arabidopsis with a C-terminal HDEL peptide for retention in the endoplasmic reticulum (SEQ ID NO:5), and the nopaline synthase terminator (SEQ ID NO:35), annotated and shown in FIG. 4 as 2×35S promoter+TMVΩ, signal peptide, $αS_1$ casein, and NOS terminator, respectively.

Further continuing this example, $TU_{1-2}$ includes a 35S short promoter containing a truncated version of the cauliflower mosaic virus promoter and the tobacco mosaic virus omega leader sequence (SEQ ID NO:31), a signal peptide (SEQ ID NO:27), the β-casein coding sequence codon optimized for expression in Arabidopsis with a C-terminal HDEL peptide for retention in the endoplasmic reticulum (SEQ ID NO:7), and the nopaline synthase terminator (SEQ ID NO:35), abbreviated and shown in FIG. 4 as 35S SHORT PROMOTER+TMVQ, SIGNAL PEPTIDE, β-CASEIN, and NOS TERMINATOR, respectively.

Further continuing this example, $TU_{1-3}$ includes the mannopine synthase promoter from *Agrobacterium tumefaciens* (SEQ ID NO:32), a signal peptide (SEQ ID NO:27), the κ-casein coding sequence codon optimized for expression in Arabidopsis with a C-terminal HDEL peptide for retention in the endoplasmic reticulum (SEQ ID NO:6), and the nopaline synthase terminator (SEQ ID NO:35), abbreviated and shown in FIG. 4 as MANNOPINE SYNTHASE PRO- MOTER (*A. TUMEFACIENS*), SIGNAL PEPTIDE, κ-CASEIN, and NOS TERMINATOR, respectively.

Further continuing this example, $TU_{1-4}$ includes the mannopine synthase promoter from *Agrobacterium tumefaciens*, a signal peptide (SEQ ID NO:32), the $αS_2$-casein coding sequence codon optimized for expression in Arabidopsis with a C-terminal HDEL peptide for retention in the endoplasmic reticulum (SEQ ID NO:8), and the nopaline synthase terminator (SEQ ID NO:35), abbreviated and shown in FIG. 4 as MANNOPINE SYNTHASE PROMOTER (*A. TUMEFACIENS*), SIGNAL PEPTIDE, $αS_2$ CASEIN, and NOS TERMINATOR, respectively.

Referring now to FIG. 5, therein is shown an example of a schematic illustration of a portion of a plasmid in Arabidopsis for a screenable marker in plants. As a specific example, FIG. 5 schematically illustrates elements of plasmids that provide for a screenable marker in plants. Transcription units depicted are components of $TUS_2$ in Arabidopsis.

The example shown in FIG. 5 depicts a transcription unit set which can be used to identify plant cells that have been transformed. The transcription unit set, abbreviated and shown in FIG. 5 as $TUS_2$, includes a single transcription unit, abbreviated and shown in FIG. 5 as $TU_{2-1}$.

Continuing this example for a portion of the plant transformation shown in FIG. 5 as an embodiment, $TU_{2-1}$ includes the nopaline synthase constitutive promoter (SEQ ID NO:28), the enhanced green fluorescence protein coding sequence modified to enhance fluorescence brightness and codon optimized for expression in Arabidopsis (SEQ ID NO:33), and the nopaline synthase terminator (SEQ ID NO:35), abbreviated and shown in FIG. 5 as NOS PROMOTER, EGFP, and NOS TERMINATOR, respectively.

As a specific example, subsequent steps in the plant transformation for creation of casein micelles in vivo in *Arabidopsis thalian*, a plasmid including $TUS_1$ and $TUS_2$ can be introduced into *Arabidopsis thaliana* cotyledons using *Agrobacterium tumefaciens* and the FAST transient expression method. Seedlings are soaked in a solution containing *Agrobacterium* two days after germination which results in some cotyledon cells being transformed. Transformed Arabidopsis cells can be identified as containing the T-DNA by observing fluorescence exhibited by the enhanced green fluorescence protein. Successfully transformed Arabidopsis cells display green fluorescence while unsuccessfully transformed cells show little or no green fluorescence.

Also as a specific example of the in vivo formation of micelles in *Arabidopsis thaliana* as an embodiment, immunogold labeling techniques can be used to identify the location and morphology of the casein micelles formed in vivo. For this example for the in vivo formation of micelles as an embodiment, embryonic tissue can be obtained from *Arabidopsis thaliana* that has been transformed with a plasmid including $TUS_1$, and optionally $TUS_2$, shown in FIG. 4 and FIG. 5, respectively. The embryonic tissue can be treated with casein-specific antibodies using immunogold labeling techniques, and imaged with transmission electron microscopy to identify the location and morphology of the micelles formed in vivo. In tissue obtained from the transformed *Arabidopsis thaliana*, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed *Arabidopsis thaliana*.

Continuing this specific example of the in vivo formation of micelles in Arabidopsis thaliana as an embodiment, protein extraction and high performance liquid chromatography (HPLC) analysis can be used to evaluate the protein composition of the casein micelles formed in vivo. In this example for the in vivo formation of micelles as an embodiment, embryonic tissue can be obtained from *Arabidopsis thaliana* that has been transformed with a plasmid including $TUS_1$, and optionally $TUS_2$, shown in FIG. 4 and FIG. 5, respectively. Proteins extracted from the embryonic tissue can be separated using HPLC and detected by ultraviolet absorbance. Proteins extracted from the transformed *Arabidopsis thaliana* tissue and subjected to HPLC analysis show peaks associated with each four proteins found in a casein micelle, including $αS_1$ casein, $αS_2$ casein, β casein, and κ casein, that display retention times similar to those reported by Bordin et al. for each of the four casein proteins found in bovine casein micelles. As a control, proteins extracted from the untransformed *Arabidopsis thaliana* tissue and subjected to HPLC analysis do not show peaks associated with any of the four casein proteins.

Further continuing this specific example of the in vivo formation of micelles in *Arabidopsis thaliana* as an embodiment, the amount of each casein protein found in micelles formed in vivo can be quantified by measuring the area under the peaks produced upon HPLC analysis. Quantification of the peaks produced upon HPLC analysis of proteins extracted from transformed *Arabidopsis thaliana* produces measurements showing that $αS_1$ casein is the most abundant, followed by β casein as the next most abundant, then $αS_2$ casein and κ casein as the least abundant casein proteins, which correlates to the relative abundances of each of the four casein proteins in bovine casein micelles as previously reported in the Handbook of Dairy Foods and Nutrition, Table 1.1.

Aspects of the disclosure can be further illustrated by a specific embodiment in which a casein micelle is assembled in vivo from its constituent proteins in soybean and further described in FIG. 6 through FIG. 9.

Referring now to FIG. 6, therein is shown an example of a schematic illustration of a portion of a plasmid in soybean. As a specific example, FIG. 6 schematically illustrates elements of plasmids that encode micellar component proteins. Transcription units depicted are components of $TUS_1$ in soybean.

In this example, FIG. 6 depicts a transcription unit set which can be used for creation of casein micelles in vivo in soybean. The transcription unit set includes one transcription unit for each of the four casein proteins found in a casein micelle, abbreviated and shown in FIGS. 4 as $TU_{1-1}$, $TU_{1-2}$, $TU_{1-3}$, and $TU_{1-4}$. The first transcription unit set is abbreviated and shown in FIG. 6 as $TUS_1$. Each of the four transcription units includes a promoter, a plant-derived N-terminal signal peptide, DNA encoding one of the four proteins found in a casein micelle, and a transcriptional terminator.

Continuing this example for a portion of the plant transformation shown in FIG. 6 as an embodiment, $TU_{1-1}$ includes a promoter from the soybean glycinin GY1 gene (SEQ ID NO:13), a signal peptide (SEQ ID NO:26), the $αS_1$ casein coding sequence codon optimized for expression in soybean (SEQ ID NO:1), and the nopaline synthase terminator (SEQ ID NO:35), abbreviated and shown in FIG. 6 as GY1 PROMOTER, SIGNAL PEPTIDE, $αS_1$ CASEIN, and NOS TERMINATOR, respectively.

Further continuing this example for a portion of the plant transformation shown in FIG. 6 as an embodiment, $TU_{1-2}$ includes the promoter from the soybean CG1 gene (SEQ ID NO:14), a signal peptide (SEQ ID NO:26), the β casein coding sequence codon optimized for expression in soybean (SEQ ID NO:3), and the nopaline synthase terminator (SEQ ID NO:35), abbreviated and shown in FIG. 6 as CG1 PROMOTER, SIGNAL PEPTIDE, β CASEIN, and NOS TERMINATOR, respectively.

Further continuing this example for a portion of the plant transformation shown in FIG. 6 as an embodiment, $TU_{1-3}$ includes the promoter from the soybean glycinin GY4 gene (SEQ ID NO:15), a signal peptide (SEQ ID NO:26), the κ casein coding sequence codon optimized for expression in soybean (SEQ ID NO:2), and the nopaline synthase terminator (SEQ ID NO:35), abbreviated and shown in FIG. 6 as GY4 PROMOTER, SIGNAL PEPTIDE, κ CASEIN, and NOS TERMINATOR, respectively.

Further continuing this example for a portion of the plant transformation shown in FIG. 6 as an embodiment, $TU_{1-4}$ includes the promoter from the soybean D-II Bowman-Birk proteinase isoinhibitor gene (SEQ ID NO:16), a signal peptide (SEQ ID NO:26), the $\alpha S_2$ casein coding sequence codon optimized for expression in soybean (SEQ ID NO:4), and the nopaline synthase terminator (SEQ ID NO:35), abbreviated and shown in FIG. 6 as D-II PROMOTER, SIGNAL PEPTIDE, $\alpha S_2$ CASEIN, and NOS TERMINATOR, respectively.

Referring now to FIG. 7, therein is shown an example of a schematic illustration of a portion of a plasmid in soybean for herbicide resistance in plants. As a specific example, FIG. 7 schematically illustrates elements of plasmids that provide for herbicide resistance in plants. Transcription units depicted are components of $TUS_2$ in soybean.

FIG. 7 is an example of a portion of the plant transformation that depicts a transcription unit set which can be used to select for plant cells that have been transformed. The transcription unit set abbreviated and shown in FIG. 7 as $TUS_2$ includes a single transcription unit abbreviated and shown in FIG. 7 as $TU_{2-1}$.

Continuing this example for a portion of the plant transformation shown in FIG. 7 as an embodiment, $TU_{2-1}$ includes nopaline synthase promoter (SEQ ID NO:28), the phosphinothricin acetyltransferase coding sequence codon optimized for expression in soybean (SEQ ID NO:34) which confers resistance to the herbicide glufosinate, and the nopaline synthase terminator (SEQ ID NO:35), abbreviated and shown in FIG. 7 as NOS PROMOTER, PHOSPHINOTHRICIN ACETYLTRANSFERASE, and NOS TERMINATOR, respectively.

Figure 8:
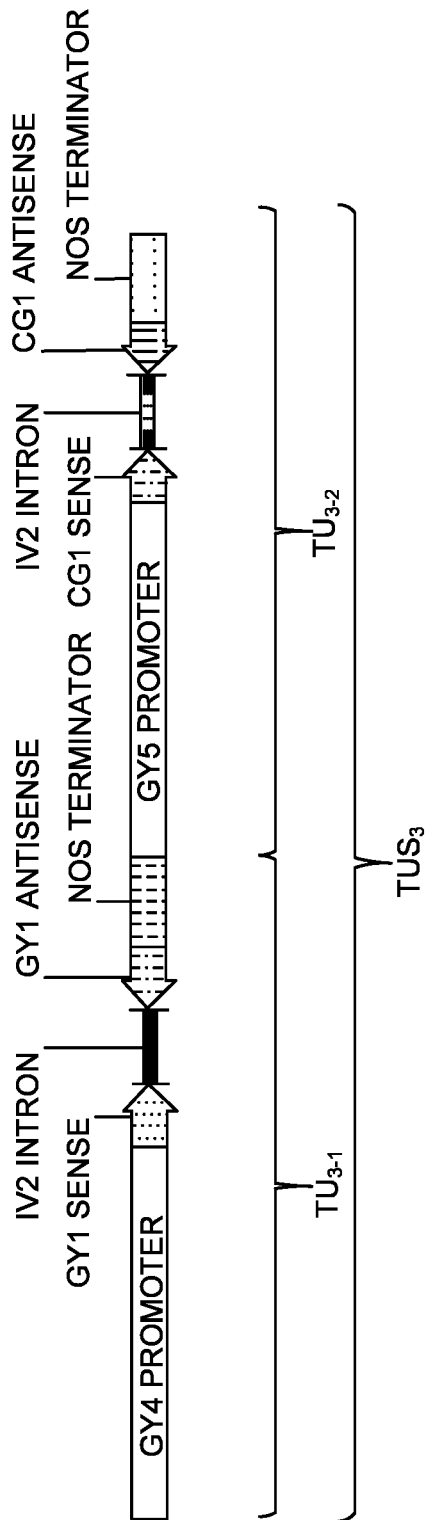
FIG. 8 is an example of a schematic illustration of a portion of the plasmid of FIG. 1 for soybean for suppression of native seed storage proteins in plants.

Referring now to FIG. 8, therein is shown an example of a schematic illustration of a portion of a plasmid in soybean for suppression of native seed storage proteins in plants. As a specific example, FIG. 8 schematically illustrates elements of plasmids that provide for suppression of native seed storage proteins in plants. Transcription units depicted are components of $TUS_3$ in soybean.

FIG. 8 is an example of a portion of the plant transformation that depicts a transcription unit set which can be used for enhancing the creation of casein micelles in vivo in soybean. The third transcription unit set abbreviated and shown in FIG. 8 as $TUS_3$ includes two transcription units abbreviated and shown in FIGS. 8 as $TU_{3-1}$ and $T_{3-}2$. The transcription of $TU_{3-1}$ and $TU_{3-2}$ produces RNA with a hairpin structure where the arms are homologous to a portion of a native soybean gene or gene family and are sufficient to cause down regulation of those native genes or gene families (not shown).

Continuing this example for a portion of the plant transformation shown in FIG. 8 as an embodiment, $TU_{3-1}$ includes a promoter from the soybean glycinin GY4 gene (SEQ ID NO:15), a portion of the soybean glycinin GY1 coding sequence that is lacking a start codon and is highly homologous among the glycinin gene family (SEQ ID NO:24), the potato IV2 intron (SEQ ID NO:25), the antisense of the soybean glycinin GY1 sequence (SEQ ID NO:17), and the nopaline synthase terminator (SEQ ID NO:35), abbreviated and shown in FIG. 8 as GY4 PROMOTER, GY1 SENSE, IV2 INTRON, GY1 ANTISENSE, and NOS TERMINATOR, respectively.

Further continuing this example for a portion of the plant transformation shown in FIG. 8 as an embodiment, $TU_{3-2}$ includes a promoter from the soybean glycinin GY5 gene (SEQ ID NO:18), a portion of the soybean β-conglycinin 1 coding sequence that is lacking a start codon and is highly homologous among the β-conglycinin gene family (SEQ ID NO:19), the potato IV2 intron (SEQ ID NO:25), the antisense of the soybean β-conglycinin 1 sequence (SEQ ID NO:20), and the nopaline synthase terminator (SEQ ID NO:35), abbreviated and shown in FIG. 8 as GY5 PROMOTER, CG1 SENSE, IV2 INTRON, CG1 ANTISENSE, and NOS TERMINATOR, respectively.

Figure 9:
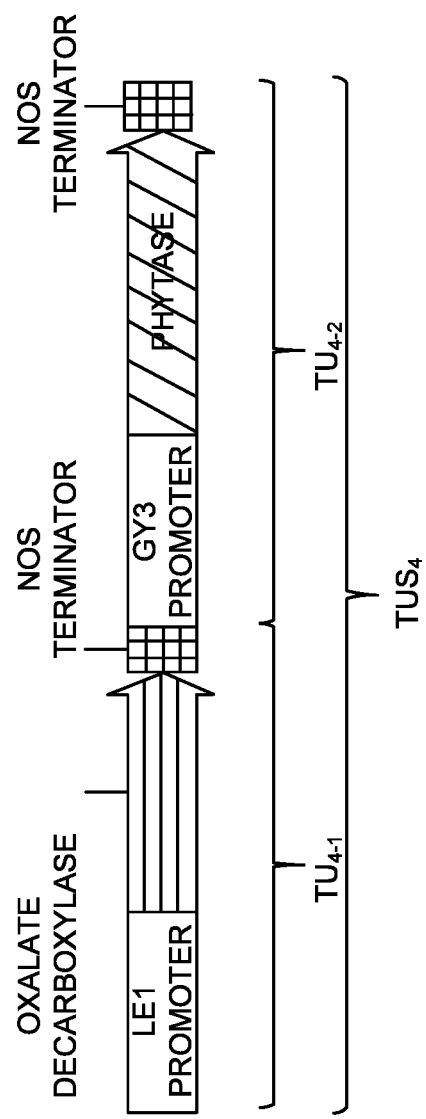
FIG. 9 is an example of a schematic illustration of a portion of a plasmid for soybean to regulate intracellular concentrations of minerals which can enhance micelle formation.

Referring now to FIG. 9, therein is shown an example of a schematic illustration of a portion of a plasmid in soybean for regulating cytoplasmic concentrations of minerals which can enhance micelle formation. As a specific example, FIG. 9 schematically illustrates elements of plasmids that regulate cytoplasmic concentrations of minerals which can enhance micelle formation. Transcription units depicted are components of $TUS_4$ in soybean.

FIG. 9 is an example of a portion of the plant transformation that depicts a transcription unit set which can be used for enhancing the creation of casein micelles in vivo in soybean. The fourth transcription unit set abbreviated and shown in FIG. 9 as $TUS_4$ includes two transcription units abbreviated and shown in FIGS. 9 as $TU_{4-1}$ and $TU_{4-2}$. Proteins encoded by $TU_{4-1}$ and $TU_4$ alter the intracellular environment in a manner that optimizes the formation of micelles in vivo.

Continuing this example for a portion of the plant transformation shown in FIG. 9 as an embodiment, $TU_{4-1}$ includes a promoter from the soybean LE1 gene (SEQ ID NO:23), a coding sequence for oxalate decarboxylase from *Flammulina velutipes* codon optimized for expression in soybean (SEQ ID NO:12), and nopaline synthase terminator (SEQ ID NO:35), abbreviated and shown in FIG. 9 as LE1 PROMOTER, OXALATE DECARBOXYLASE CDS, and NOS TERMINATOR, respectively.

Further continuing this example for a portion of the plant transformation shown in FIG. 9 as an embodiment, $TU_{4-2}$ includes the glycinin GY3 promoter (SEQ ID NO:30), the coding sequence for a soybean phytase enzyme (SEQ ID NO:11), and the nopaline synthase terminator (SEQ ID NO:35), abbreviated and shown in FIG. 9 as GY3 PROMOTER, PHYTASE, and NOS TERMINATOR, respectively.

In this example, subsequent steps in the plant transformation for creation of casein micelles in vivo in soybean, a plasmid including $TUS_1$, $TUS_2$, and optionally $TUS_3$, and optionally $TUS_4$, shown in FIG. 6, FIG. 7, FIG. 8, and FIG. 9, respectively, can be introduced into soybean callus using standard biolistic transformation methods. Transformed soybean plants can be selected on a medium containing glufosinate herbicide, and the genomes of transformed soybean plants can be screened for insertion of the plasmid using standard PCR mapping methods. Transformed soybean plants including $TUS_1$, $TUS_2$, and optionally $TUS_3$, and optionally $TUS_4$ in their genome can be transferred to a greenhouse for seed production.

In the example of the in vivo formation of micelles in soybean as an embodiment, immunogold labeling techniques can be used to identify the location and morphology of the casein micelles formed in vivo. As it relates to this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. The tissue can be treated with casein-specific antibodies using standard immunogold labeling techniques, and imaged with transmission electron microscopy to identify the location and morphology of the micelles formed in vivo. In tissue obtained from the transformed soybean plants, the casein micelles are visualized as gold-antibody labeled subcellular structures that range in size from 50 nm to 600 nm, which is similar to the size of bovine casein micelles. As a control, no casein micelles are visualized using immunogold labeling techniques in tissue obtained from untransformed soybean plants.

Continuing this example of the in vivo formation of micelles in soybean as an embodiment, protein extraction and polyacrylamide gel electrophoresis analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue and subjected to polyacrylamide gel electrophoresis analysis show bands on the polyacrylamide gel corresponding in size to each of the four casein proteins found in a casein micelle, including $\alpha S_1$ casein, $\alpha S_2$ casein, β casein, and κ casein. As a control, proteins extracted from untransformed soybean plant tissue and subjected to polyacrylamide gel electrophoresis analysis do not show bands on the polyacrylamide gel corresponding to the four casein proteins.

Further continuing this example of the in vivo formation of micelles in soybean as an embodiment, protein extraction and HPLC analysis can be used to evaluate the protein composition of the casein micelles formed in vivo. For this example for the in vivo formation of micelles as an embodiment, tissue can be obtained from soybean plants that have been transformed with a plasmid including $TUS_1$, $TUS_2$, and optionally $TUS_3$, and optionally $TUS_4$, shown in FIG. 6, FIG. 7, FIG. 8, and FIG. 9, respectively. Proteins extracted from the transformed soybean plant tissue can be separated using HPLC and detected by ultraviolet absorbance. Proteins extracted from the transformed soybean plant tissue and subjected to HPLC analysis show peaks associated with each four proteins found in a casein micelle, including $\alpha S_1$ casein, $\alpha S_2$ casein, β casein, and κ casein, that display retention times similar to those reported by Bordin et al. for each of the four casein proteins found in bovine casein micelles. As a control, proteins extracted from the untransformed soybean plant tissue and subjected to HPLC analysis do not show peaks associated with the four casein proteins.

Further continuing this example of the in vivo formation of micelles in soybean as an embodiment, the amount of each casein protein found in micelles formed in vivo can be quantified by measuring the area under the peaks produced upon HPLC analysis. Quantification of the peaks produced upon HPLC analysis of proteins extracted from transformed soybean plant tissue produces measurements showing that $\alpha S_1$ casein is the most abundant, followed by β casein as the next most abundant, then $\alpha S_2$ casein and κ casein as the least abundant casein proteins, which correlates to the relative abundances of each of the four casein proteins in bovine casein micelles as previously reported in the Handbook of Dairy Foods and Nutrition, Table 1.1.

Further continuing this example of the in vivo formation of micelles in soybean as an embodiment, RNA analysis can be used to evaluate the suppression of native soybean seed genes during the formation of casein micelles in vivo. For this example for the in vivo formation of micelles as an embodiment, soybean plants that have been transformed with a plasmid including $TUS_1$, $TUS_2$, $TUS_3$, and optionally $TUS_4$, shown in FIG. 6, FIG. 7, FIG. 8, and FIG. 9, respectively, can be grown to the flowering stage in a greenhouse and soybean embryos removed from the flowering seed pods at 35 days using standard dissection techniques. The expression levels of native soybean seed genes can be analyzed using standard techniques for RNA extraction and sequencing. RNA analysis of the embryos from transformed soybean plants show at least a 10% reduction in the expression of one or more of the native soybean seed genes, including genes in the glycinin family (Glyma.03g163500, Glyma.19g164900, Glyma.10g037100, Glyma.13g123500, Glyma.19g164800) and genes in the β-conglycinin family (Glyma.10g246300, Glyma.20g148400, Glyma.20g148300, Glyma.20g146200, Glyma.20g148200, Glyma.10g246500, Glyma.10g028300, Glyma.02g145700). As a control, RNA analysis of embryos from untransformed soybean plants do not show a reduction in the expression of native soybean seed genes.

Further continuing this example of the in vivo formation of micelles in soybean as an embodiment, commercially available assays and X-ray fluorescence techniques can be used to evaluate calcium oxalate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9, respectively, can be grown to the flowering stage in a greenhouse and soybean embryos removed from the flowering seed pods at 27 days using standard dissection techniques. The oxalate concentration can be measured using commercially available assays, and the calcium concentration can be measured using X-ray fluorescence. Embryos from transformed soybean plants show at least a 5% reduction in oxalate concentration and at least a 4% increase in calcium concentration as compared to control embryos from untransformed soybean plants, indicating that embryos from transformed soybean plants have at least 4% more available calcium compared to embryos from untransformed soybean plants.

Further continuing this example of the in vivo formation of micelles in soybean as an embodiment, commercially available assays can be used to evaluate phosphate levels during the formation of casein micelles in vivo. As it relates to this example for the in vivo formation of micelles as an embodiment, soybean plants that have been transformed with a plasmid including $TUS_1$, $TUS_2$, and optionally $TUS_3$, and $TUS_4$, shown in FIG. 6, FIG. 7, FIG. 8, and FIG. 9., respectively, can be grown to the flowering stage in a greenhouse and soybean embryos removed from the flowering seed pods at 27 days using standard dissection techniques. Embryos can be ground with a mortar and pestle, sonicated and centrifuged to produce a supernatant that can be tested for phosphatase levels using commercially available assays. Embryos from transformed soybean plants show at least a 5% increase in phosphatase levels as compared to control embryos from untransformed soybean plants, indicating that embryos from transformed soybean plants have at least 5% more available phosphate compared to embryos from untransformed soybean plants.

Figure 10:
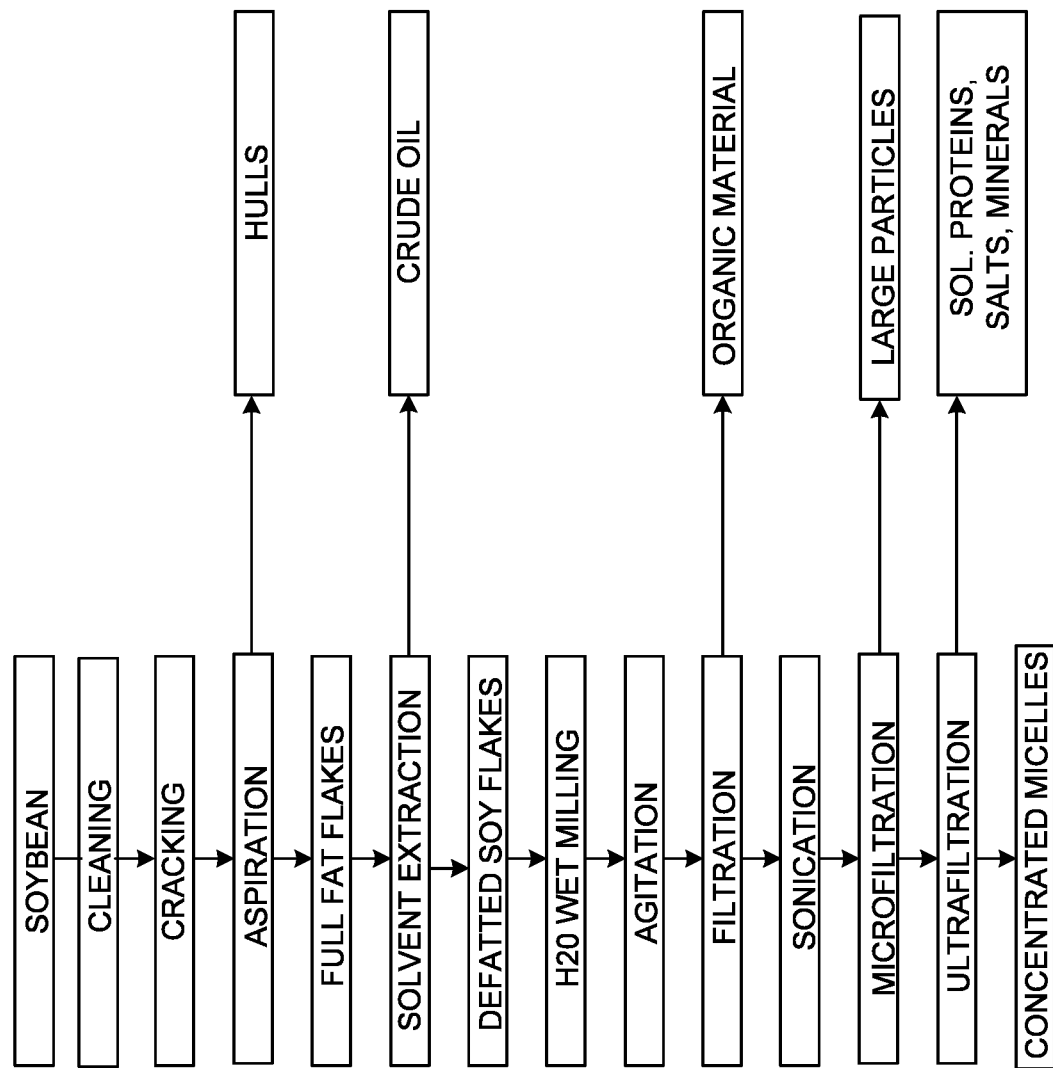
FIG. 10 is an example of a flow for the purification of micelles formed in vivo in soybean.

Aspects of the disclosure can be further illustrated by a specific embodiment in which micelles produced in vivo are purified as further described in FIG. 10.

Referring now to FIG. 10, therein is shown an example of a flow for the purification of micelles formed in vivo in soybean. Also, the flow in FIG. 10 is an example of isolating a recombinant micelle. Further in this example, FIG. 10 depicts a process where casein micelles produced in soybeans are purified from the plant tissue in a way that the micelles are still functional after the purification. The input material for the purification process is dried soybeans harvested from plants that have been transformed with a plasmid containing all four transcription unit sets, $TUS_1$, $TUS_2$, $TUS_3$, and $TUS_4$, described in FIG. 6, FIG. 7, FIG. 8, and FIG. 9, respectively. The input material for the purification process is shown in FIG. 10 and depicted as a rectangle enclosing the word "SOYBEAN".

Continuing this example of the purification of micelles formed in vivo in soybean as an embodiment, the hulls are removed from the dried soybeans in a series of steps including cleaning, cracking, and aspiration, shown in FIG. 10 and depicted as rectangles enclosing the words "CLEANING", "CRACKING" and "ASPIRATION". In this embodiment, the hulls do not contain useful amounts of casein micelles and are discarded, shown in FIG. 10 and depicted as an arrow pointing to a rectangle enclosing the word "HULLS".

Further continuing this example of the purification of micelles formed in vivo in soybean as an embodiment, the remaining material is flaked to increase the surface area and allow for faster aqueous or solvent infiltrations. The resulting flaked material is shown in FIG. 10 and depicted as a rectangle enclosing the words "FULL FAT FLAKES".

Further continuing this example of the purification of micelles formed in vivo in soybean as an embodiment, the flaked material is then defatted with hexane using standard defatting equipment and solvent extraction techniques, shown in FIG. 10 and depicted as a rectangle enclosing the words "SOLVENT EXTRACTION". Defatting can occur using any standard hexane based solvent, followed by desolventizing using flash or vapor-based processes. The resulting oil is removed, shown in FIG. 10 and depicted as an arrow pointing to a rectangle enclosing the words "CRUDE OIL", leaving behind the defatted flakes, shown in FIG. 10 and depicted as an arrow pointing to a rectangle enclosing the words "DEFATTED SOY FLAKES".

Further continuing this example of the purification of micelles formed in vivo in soybean as an embodiment, the defatted flakes are then mixed with water and wet milled, shown in FIG. 10 and depicted as an arrow pointing to a rectangle enclosing the words "H2O WET MILLING". The milling process pulverizes the defatted flakes which releases the casein micelles and allows the micelles to come into contact with an aqueous medium. In addition to the milling process, the defatted flakes are also vigorously agitated to assist in the release of casein micelles into the water, shown in FIG. 10 and depicted as an arrow pointing to a rectangle enclosing the word "AGITATION". The milling process and vigorous agitation of the defatted flakes yields a slurry where soybean material has been finely ground and many of the casein micelles have been released into suspension in the water (not shown). Additionally, many other proteins and carbohydrates are also dissolved in the water (not shown). In some embodiments, wet milling is done using perforated disc or colloid continuous flow mills.

Further continuing this example of the purification of micelles formed in vivo in soybean as an embodiment, the slurry is fed through a series of mesh screens to remove larger particles from the casein micelles, shown in FIG. 10 and depicted as an arrow pointing to a rectangle enclosing the word "FILTRATION". In this embodiment, the slurry is first passed through a screen with 5 mm sieve openings (not shown), and then is passed through a screen with 0.5 mm sieve openings (not shown). The material trapped by the screens is discarded, shown in FIG. 10 and depicted as an arrow pointing to a rectangle enclosing the words "ORGANIC MATERIAL".

Further continuing this example of the purification of micelles formed in vivo in soybean as an embodiment, the remaining material in the slurry that passed through both screens is then sonicated to break up aggregates of casein micelles such that the majority of micelles are not contacting other micelles, shown in FIG. 10 and depicted as an arrow pointing to a rectangle enclosing the word "SONICATION". In some embodiments, continuous flow sonication with multiple sonicators in parallel are used to maximize flow rates.

Further continuing this example of the purification of micelles formed in vivo in soybean as an embodiment, after sonication the slurry is passed through a 2 μm microfiltration unit to eliminate larger particles while allowing casein micelles to pass through, shown in FIG. 10 and depicted as an arrow pointing to a rectangle enclosing the word "MICROFILTRATION". The material trapped by the microfiltration unit is discarded, shown in FIG. 10 and depicted as an arrow pointing to a rectangle enclosing the words "LARGE PARTICLES". The remaining material that passed through the microfiltration unit is largely composed of casein micelles as well as dissolved proteins, salts and carbohydrates (not shown).

Further continuing this example of the purification of micelles formed in vivo in soybean as an embodiment, the material that passed through the microfiltration unit is then processed with an ultrafiltration unit that allows dissolved molecules lower than 100 nm in diameter to pass through while retaining casein micelles, shown in FIG. 10 and depicted as an arrow pointing to a rectangle enclosing the words "ULTRAFILTRATION". In some embodiments, continuous flow ultrafiltration with multiple filters in parallel are used to maximize flow rates. The soluble proteins, salts and minerals that passed through the ultrafiltration unit are discarded, shown in FIG. 10 and depicted as an arrow pointing to a rectangle enclosing the words "SOL. PROTEINS, SALTS, MINERALS".

Further continuing this example of the purification of micelles formed in vivo in soybean as an embodiment, the final output from this process is an aqueous liquid where the most common component after water is casein micelles, shown in FIG. 10 and depicted as an arrow pointing to a rectangle enclosing the words "CONCENTRATED MICELLES". These micelles (not shown) retain their shape and function such that they can be used in downstream processes such as in making synthetic milk or cheese.

As additional examples for FIG. 10, a method of isolating recombinant micelles from a seed of a plant produced can include cleaning, and deshelling or dehulling seeds, flaking cleaned seeds to 0.005-0.02 inch thickness, solvent extraction of oil from the flake, desolventizing the flake without cooking and collecting the defatted, clean flake, separating micelles into an aqueous slurry by hydrating, agitating and wet milling the flake, passing the slurry through a series of mesh screens to remove particulate above 0.5 mm in size and collecting the permeate, sonication of the permeate from previous step, microfiltration of the product from previous step to remove particulate above 2 um in size, ultrafiltration of the permeate from previous step using a device that allows particles >100 nm in diameter to pass through in the ultrafiltration permeate, collecting the retentate of previous step which contains concentrated recombinant micelles.

Continuing with this example, the method of isolating recombinant micelles from a seed further includes centrifuging the retentate of a previous step to separate the micelles from the remainder of the retentate. Also the method continues from the ultrafiltration step to passing the slurry through an ultrafiltration device and collecting a permeate containing protein and other molecules and a retentate containing micelles and thereafter adding a diafiltration fluid to the retentate at substantially the same rate that the permeate is collected and passing said retentate through the ultrafiltration device. Yet further the method continues where the seed is milled from at least one plant selected from the group of plants consisting of maize, rice, sorghum, cowpeas, soybeans, cassava, coyam, sesame, peanuts, peas, cotton and yams.

The resulting method, process, apparatus, device, product, and system is cost-effective, highly versatile, and accurate, and can be implemented by adapting components for ready, efficient, and economical manufacturing, application, production, and utilization. Another important aspect of an embodiment of the present disclosure is that it valuably supports and services the historical trend of reducing costs, simplifying systems, and increasing yield.

These and other valuable aspects of the embodiments of the present disclosure consequently further the state of the technology to at least the next level. While the disclosure has been described in conjunction with a specific best mode, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of expressing casein protein in a soybean plant, comprising:
   a) expressing casein protein in a plant cell;
   b) accumulating casein protein in a protein storage vacuole; and
   c) suppressing expression of a native plant protein or a native plant peptide in the plant cell, wherein the suppressing expression of the native plant protein or native plant peptide in the plant cell increases expression of casein protein in the plant cell.

2. The method in claim 1, wherein the casein protein is a bovine k-casein.

3. The method in claim 1, wherein the casein protein is a bovine αS1-casein.

4. The method in claim 1, wherein the casein protein is a bovine αS2-casein.

5. The method in claim 1, wherein the casein protein is a bovine β-casein.

6. The method in claim 1, wherein suppressing expression of a native plant or native plant peptide comprises using RNAi to target messenger RNA of the native plant protein or the native plant peptide.

7. The method in claim 1, wherein the native plant protein or the native plant peptide is β-conglycinin.

8. The method in claim 1, wherein the native plant protein or the native plant peptide is glycinin.

* * * * *